(12) United States Patent
Hourtash

(10) Patent No.: US 9,844,415 B2
(45) Date of Patent: Dec. 19, 2017

(54) SYSTEMS AND METHODS FOR FACILITATING ACCESS TO EDGES OF CARTESIAN-COORDINATE SPACE USING THE NULL SPACE

(71) Applicant: Intuitive Surgical Operations, Inc., Sunnyvale, CA (US)

(72) Inventor: Arjang M. Hourtash, Santa Clara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 15/193,924

(22) Filed: Jun. 27, 2016

(65) Prior Publication Data

US 2016/0302875 A1    Oct. 20, 2016

Related U.S. Application Data

(63) Continuation of application No. 14/218,871, filed on Mar. 18, 2014, now Pat. No. 9,375,284.
(Continued)

(51) Int. Cl.
*B25J 9/16* (2006.01)
*A61B 34/30* (2016.01)
(Continued)

(52) U.S. Cl.
CPC .............. *A61B 34/30* (2016.02); *A61B 34/37* (2016.02); *B25J 9/1607* (2013.01); *B25J 9/1643* (2013.01);
(Continued)

(58) Field of Classification Search
CPC ....................................................... A61B 34/30
(Continued)

(56) References Cited

U.S. PATENT DOCUMENTS

| 5,430,643 A | 7/1995 | Seraji |
| 5,499,320 A | 3/1996 | Backes et al. |

(Continued)

FOREIGN PATENT DOCUMENTS

| EP | 2332484 A2 | 6/2011 |
| EP | 1885273 B1 | 2/2012 |

(Continued)

OTHER PUBLICATIONS

International Search Report and Written opinion for Application No. PCT/US14/31103, dated Jul. 29, 2014, 17 pages.
(Continued)

*Primary Examiner* — David S Luo
(74) *Attorney, Agent, or Firm* — Schwegman Lundberg & Woessner, P.A.

(57) ABSTRACT

Devices, systems, and methods for providing increased range of movement of the end effector of a manipulator arm having a plurality of joints with redundant degrees of freedom. Methods include defining a position-based constraint within a joint space defined by the at least one joint, determining a movement of the joints along the constraint within a null-space and driving the joints according to a calculated movement to effect the commanded movement while providing an increased end effector range of movement, particularly as one or more joints approach a respective joint limit within the joint space.

20 Claims, 20 Drawing Sheets

Related U.S. Application Data

(60) Provisional application No. 61/800,381, filed on Mar. 15, 2013.

(51) Int. Cl.
  *B25J 18/00* (2006.01)
  *A61B 34/37* (2016.01)
  *A61B 90/00* (2016.01)

(52) U.S. Cl.
  CPC ........... *B25J 9/1666* (2013.01); *B25J 18/007* (2013.01); *A61B 90/03* (2016.02); *G05B 2219/40371* (2013.01); *G05B 2219/40474* (2013.01)

(58) Field of Classification Search
  USPC .................. 318/568.11, 568.1, 567, 560
  See application file for complete search history.

(56) References Cited

U.S. PATENT DOCUMENTS

| | | | |
|---|---|---|---|
| 5,784,542 A * | 7/1998 | Ohm | B25J 3/04 700/247 |
| 8,004,229 B2 | 8/2011 | Nowlin et al. | |
| 9,107,683 B2 | 8/2015 | Houtash et al. | |
| 9,345,544 B2 | 5/2016 | Hourtash et al. | |
| 9,375,284 B2 | 6/2016 | Hourtash | |
| 9,492,235 B2 | 11/2016 | Hourtash et al. | |
| 2007/0287884 A1 | 12/2007 | Schena | |
| 2012/0123441 A1 | 5/2012 | Au et al. | |
| 2014/0358161 A1 | 12/2014 | Hourtash et al. | |

FOREIGN PATENT DOCUMENTS

| | | |
|---|---|---|
| WO | WO-2007005555 A2 | 1/2007 |
| WO | WO-2007030173 A1 | 3/2007 |
| WO | WO-2010030463 A1 | 3/2010 |
| WO | WO-2013078529 A1 | 6/2013 |
| WO | WO-2013181503 A1 | 12/2013 |
| WO | WO-2013181507 A1 | 12/2013 |
| WO | WO-2013181516 A1 | 12/2013 |
| WO | WO-2014028703 A1 | 2/2014 |
| WO | WO-2014146119 A1 | 9/2014 |

OTHER PUBLICATIONS

Notice of Allowance dated Feb. 29, 2016 for U.S. Appl. No. 14/218,871, filed Mar. 18, 2014, 8 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

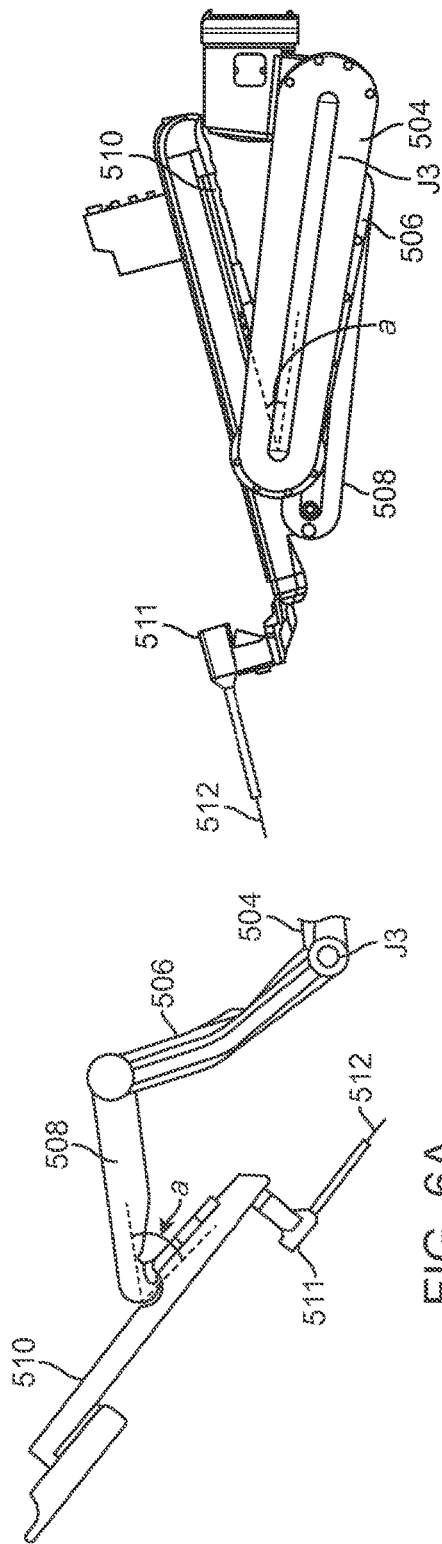
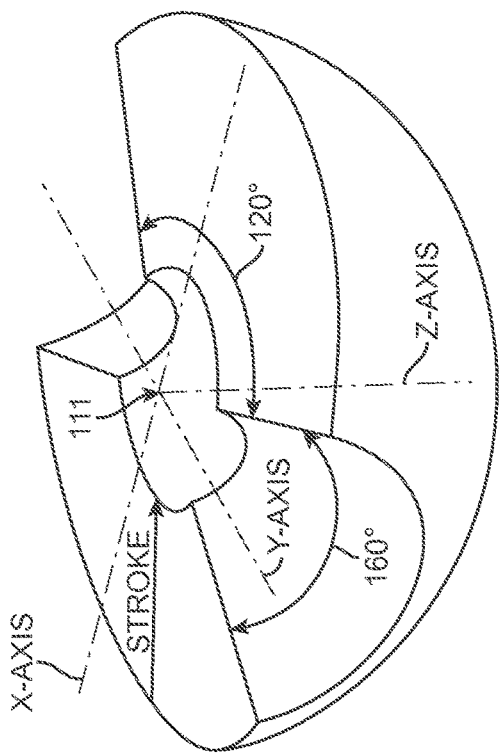

SYSTEMS AND METHODS FOR FACILITATING ACCESS TO EDGES OF CARTESIAN-COORDINATE SPACE USING THE NULL SPACE

CROSS-REFERENCES TO RELATED APPLICATIONS

This application is a continuation of and claims the benefit of priority under 35 U.S.C. §120 to U.S. patent application Ser. No. 14/218,871, filed on Mar. 18, 2014, claims the benefit of priority under 35 U.S.C. §119(e) to U.S. Provisional Patent Application Ser. No. 61/800,381, filed on Mar. 15, 2013, the benefit of priority of each of which is claimed hereby, and each of which are incorporated by reference herein in its entirety.

The present application is generally related to the following commonly-owned applications: U.S. application Ser. No. 12/494,695 filed Jun. 30, 2009, entitled "Control of Medical Robotic System Manipulator About Kinematic Singularities;" U.S. application Ser. No. 12/406,004 filed Mar. 17, 2009, entitled "Master Controller Having Redundant Degrees of Freedom and Added Forces to Create Internal Motion;" U.S. application Ser. No. 11/133,423 filed May 19, 2005 (U.S. Pat. No. 8,004,229), entitled "Software Center and Highly Configurable Robotic Systems for Surgery and Other Uses;" U.S. application Ser. No. 10/957,077 filed Sep. 30, 2004 (U.S. Pat. No. 7,594,912), entitled "Offset Remote Center Manipulator For Robotic Surgery;" and U.S. application Ser. No. 09/398,507 filed Sep. 17, 1999 (U.S. Pat. No. 6,714,839), entitled "Master Having Redundant Degrees of Freedom;" U.S. Provisional Application No. 61/654,755 filed Jun. 1, 2012, entitled "Manipulator Arm-to-Patient Collision Avoidance Using a Null-Space;" and U.S. Provisional Application No. 61/654,773 filed Jun. 1, 2012, entitled "System and Methods for Avoiding Collisions Between Manipulator Arms Using a Null-Space," the disclosures of which are incorporated herein by reference in their entireties.

BACKGROUND OF THE INVENTION

The present invention generally provides improved surgical and/or robotic devices, systems, and methods.

Minimally invasive medical techniques are aimed at reducing the amount of tissue which is damaged during diagnostic or surgical procedures, thereby reducing patient recovery time, discomfort, and deleterious side effects. Millions of "open" or traditional surgeries are performed each year in the United States; many of these surgeries can potentially be performed in a minimally invasive manner. However, only a relatively small number of surgeries currently use minimally invasive techniques due to limitations in surgical instruments, and techniques, and the additional surgical training required to master them.

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a three-dimensional image of the surgical site on a suitable viewer or display, the surgeon performs the surgical procedures on the patient by manipulating master control input devices, which in turn control the motion of robotic instruments. The robotic surgical instruments can be inserted through small, minimally invasive surgical apertures to treat tissues at surgical sites within the patient, often the trauma associated with accessing for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

The servomechanism used for telesurgery will often accept input from two master controllers (one for each of the surgeon's hands) and may include two or more robotic arms or manipulators. Mapping of the hand movements to the image of the robotic instruments displayed by the image capture device can help provide the surgeon with accurate control over the instruments associated with each hand. In many surgical robotic systems, one or more additional robotic manipulator arms are included for moving an endoscope or other image capture device, additional surgical instruments, or the like.

A variety of structural arrangements can be used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Pat. Nos. 6,758,843; 6,246,200, and 5,800,423, the full disclosures of which are incorporated herein by reference. These linkages often make use of a parallelogram arrangement to hold an instrument having a shaft. Such a manipulator structure can constrain movement of the instrument so that the instrument shaft pivots about a remote center of spherical rotation positioned in space along the length of the rigid shaft. By aligning this center of rotation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially dangerous forces against the abdominal wall. Alternative manipulator structures are described, for example, in U.S. Pat. Nos. 6,702,805; 6,676,669; 5,855,583; 5,808,665; 5,445,166; and 5,184,601, the full disclosures of which are incorporated herein by reference.

While the new robotic surgical systems and devices have proven highly effective and advantageous, still further improvements would be desirable. For example, a manipulator arm may include additional redundant joints to provide increased movements or configurations under certain conditions. When moving surgical instruments within a minimally invasive surgical site, however, joints may become poorly conditioned or configured in such a way that limits the ability of the manipulator arm to access its full range of motion, particularly when pivoting instruments about minimally invasive apertures through large angular ranges. In such cases, movement of the joints may inadvertently result in limited joint motion of one or more joints upon approaching an associated joint limit, thereby reducing the dexterity of the manipulator arm. Alternative manipulator structures have been proposed which employ software control over a highly configurable kinematic manipulator joint set to restrain pivotal motion to the insertion site while inhibiting inadvertent manipulator/manipulator contact outside the patient (or the like). These highly configurable "software center" surgical manipulator systems may provide significant advantages, but may also present challenges. In particular, the mechanically constrained remote-center linkages may have safety advantages in some conditions. Additionally, the wide range of configurations of the numerous joints often included in these manipulators may result in the manipulators being difficult to manually set-up in a configuration that is desirable for a particular procedure. Nonetheless, as the range of surgeries being performed using tele-surgical systems continues to expand, there is an increasing demand for expanding the available configurations and the range of motion of the instruments within the patient. Unfortunately, both of these changes can increase the challenges associated with the motion of the manipulators outside the body, and can also increase the importance of avoiding combinations of joint states that unnecessarily limit the range of motion of the manipulator arm.

For these and other reasons, it would be advantageous to provide improved devices, systems, and methods for surgery, robotic surgery, and other robotic applications, and it would be particularly beneficial if these improved technologies provided the ability to provide more consistent movement of the manipulator arm to improve range of motion of the instruments for at least some tasks and without significantly increasing the size, mechanical complexity, or costs of these systems, and while maintaining or improving their dexterity.

BRIEF SUMMARY OF THE INVENTION

The present invention generally provides improved robotic and/or surgical devices, systems, and methods. In many embodiments, the invention will employ highly configurable surgical robotic manipulators. These manipulators, for example, may have more degrees of freedom of movement than the associated surgical end effectors have within a surgical workspace. A robotic surgical system in accordance with the present invention typically includes a manipulator arm supporting a robotic surgical instrument and a processor to calculate coordinated joint movements for manipulating an end effector of the instrument. The joints of the robotic manipulators supporting the end effectors allow the manipulator to move throughout a range of different configurations for a given end effector position and/or a given pivot point location. In one aspect, the invention provides improved range of motion and maneuverability of the manipulator arm by defining a positioned-based constraint within a joint-space of two or more joints of the manipulator and moving the joints of the manipulator within a null-space of the Jacobian based on the position-based constraint to provide increased range of movement for one or more joints, particularly near the edges or joint limits of the one or more joints.

In certain aspects, the robotic surgical system utilizes holonomic or position-based paths that are defined within a Cartesian-coordinate space of the manipulator arm and correspond to a desired movement of one or more joints of a manipulator arm having a distal end effector. The Cartesian-coordinate space may be defined as the space of positions and orientations of any desired control frame. The control frame may be the tool-tip, a reference attached to the manipulator body but not at the tool tip (e.g. another part of the tool), a reference not attached to the manipulator body but that is associated or moves with one of the links (e.g. formation flying with an imaginary point which is attached the manipulator) or a reference that is not attached or associated with the manipulator (e.g. attached to a target anatomy), one possible use of which would be a camera control. Virtual potential fields may be calculated within the joint-space or Cartesian-coordinate space and used to determine joint velocities of the joints to effect movement of one or more joints of the manipulator within a null-space toward the position-based constraint or paths thereby providing improved range of movement of the one or more joints while maintaining a desired position or state of an end effector. This approach allows for improved control over the movement of one or more joints within a null-space, particularly in a manipulator arm utilizing a Jacobian based controller in which the primary calculations of the one or more joints are based on velocities rather than positions.

In one aspect, the joint-space may be defined by the hardstops of the joints of the manipulator arm. The end-effector or tool-tip in the Cartesian-coordinate space can move in a variety of ways depending on how the null-space is used. Without use of the null-space, the same Cartesian-coordinate space position may be close or far from the joint space limits (e.g. hardstops). Therefore, for the same Cartesian-coordinate space positions, the manipulator movement can be calculated so as to slide along the null motion manifold away from the joint space limits or hardstops, thereby ensuring that the full range of available Cartesian-coordinate space positions are utilized. One advantage of these aspects is that when driving the manipulator arm in the Cartesian-coordinate space, the null-space, which is an attribute of the mapping between the joint and Cartesian-coordinate space (e.g. indirectly mapping between the control frame and the hardstops) can be used to maximize utility.

In certain aspects, the position-based constraint is defined as one or more feature or paths within the joint space, the feature/paths corresponding to movement of the joints within a null-space such that a state of a distal portion of the manipulator arm is maintained. The position-based constraints may vary according to the kinematics of the joints of a given manipulator arm so as to provide increased range of joint movement for the manipulator arm. The one or more paths may comprise a series of curves or surfaces representing along which movement of at least two joints is within a null-space of the Jacobian, the shape of the paths, curves or surfaces being dependent on the kinematics of the manipulator, and in particular the relationship between the joints defining the joint-space in which the constraint is defined. In many of the embodiments described herein, the series of curves or surfaces are substantially parallel, the curves being along an outer pitch joint axis of the joint-space, the curves each opening toward a pitch forward direction.

In one aspect, the path may include a single path (e.g. curve or surface) that is translated or modified in response to a position of at least one joint within the joint-space. For example, the path may be a single curve/surface that is translated along the outer pitch axis as a state of the pitch joint moves along the outer pitch joint axis. In certain embodiments, the potential field defined in the joint-space may vary according to the position of the path within the joint-space. For example, as a curve or surface translates toward the pitch forward from an origin of the joints space, the surrounding potential field pulls the subject joints towards one or both of a non-displaced lateral pivot joint state lateral pivot or minimum forward pitch, while as the path curve translates in the backward pitch direction from the origin of the sub-space, the potential field pulls the joint states toward one or both of a displaced lateral pivot joint and/or a non-displaced pitch joint state.

In some embodiments, a manipulator arm may include additional redundant joints to allow for various types of movement, such as a reconfiguration movement in response to a user command or an external manual articulation of a joint. Rather than relying on robotic devices that are mechanically constrained to pivot a tool about a fixed point in space, or robotic devices having passive joints which passively pivot about the tissues of a minimally invasive aperture, embodiments of the present invention may calculate a motion that includes pivoting a link of the manipulator linkage about an aperture site. The degrees of freedom of the robotic linkages supporting the end effectors can allow the linkage to move throughout a range of configurations for a given end effector position, and the systems may drive the linkages to configurations which inhibit collisions involving one or more moving robotic structures. Set-up of highly flexible robotic linkages can be facilitated by processors which drive one or more joints of the linkage while the linkage is being manually positioned.

In some embodiments, the invention allows for movement of the manipulator arm to be directed towards a pre-determined set of constraints when moving to effect one more tasks, such as a desired end effector movement, a reconfiguration movement or various others movements. It should be noted that the manipulator arm need not be mechanically "locked" to the set of constraints, but rather the constraints can be utilized to direct movement of one or more joints of the manipulator arm when moving according to one or more commanded movements. The manipulator arm may include various movements or modes of operation in which joint movements of the manipulator arm are not limited by the defined constraints.

In general, commanded movement of the manipulator arm to effect movement of the distal end effector utilizes movement of all the joints of the manipulator arm. Various other types of movement, such as a commanded reconfiguration movement may utilize the same joints as used in manipulation of the end effector or may include various other selected joints or sets of joints. When effecting movement of a manipulator arm having redundant degrees of freedom, the motion of the joints according to one or more of these types of movement may result in unnecessary or unpredictable movement of the manipulator arm. In addition, movement of an upper portion of a manipulator arm may unnecessarily limit the available range of motion of an adjacent manipulator arm, particularly when adjacent manipulator arms are driven according to a collision avoidance movement in addition to an end effector manipulation movement. To provide improved movement of the manipulator arms, the redundant degrees of freedom may be used to determine one or more constraints to direct movement of the joints toward configurations having increased range of movement for one or more joints. The constraints may be defined in either the joint-space using joint velocities or within Cartesian-coordinate space using positions.

In one aspect, the movement of a manipulator arm having redundant degrees of freedom utilized primary calculations based on joint velocities, such as by using a Jacobian based controller. The system may define a set of holonomic or position based constraints, such as one or more paths or curves, in either the joint-space or the Cartesian-coordinate space. The constraints may be used to develop an artificial potential field to "pull" or direct the movement of the manipulator arm towards using movement of the joints within a null-space of the Jacobian. This allows the one or more joints of the manipulator arm to move so as to increase the range of movement of one or more joints within the joint-space, while maintaining a desired state of the end effector during commanded end effector movements.

In various embodiments, the invention provides a robotic system comprising a manipulator assembly for robotically moving a distal end effector relative to a proximal base. The manipulator assembly has a plurality of joints, the joints providing sufficient degrees of freedom to allow a range of joint states for an end effector state. An input receives a command to effect a desired movement of the end effector. A processor couples the input to the manipulator assembly and includes a first module and a second module. The first module is configured to help calculate movements of the joints in response to the command so as to move the end effector with the desired movement. The second module is configured to help drive at least one of the joints in response to an external articulation of another joint of the manipulator assembly, such as a clutch mode.

In certain aspects of the present invention, a redundant degrees of freedom (RDOF) surgical robotic system with manipulate input is provided. The RDOF surgical robotic system includes a manipulator assembly, one or more user input devices, and a processor with a controller. A manipulator arm of the assembly has a plurality of joints providing sufficient degrees of freedom that allow a range of joint states for a given end effector state. In response to a received reconfiguration command entered by a user, the system calculates velocities of the plurality of joints within a null-space. The joints are driven according to the reconfiguration command and the calculated movement so as to maintain the desired state of the end effector. Typically, in response to receiving a manipulation command to move the end effector with a desired movement, the system calculates end effector displacing movement of the joints by calculating joint velocities within a null-perpendicular-space of the Jacobian orthogonal to the null-space, and drives the joints according to the calculated movement to effect the desired end effector movement. To provide increased maneuverability and range of motion for the various other types of movements described above, the system may include a revolute proximal most joint that affects the pitch of a distal instrument shaft of the manipulator and/or a distal revolute joint coupling an instrument to a proximal portion of the manipulator arm that effects a pivotal movement of the instrument shaft laterally from a plane through which the portion of the manipulator arm proximal of the distal revolute joint extends. These joints may be utilized in any of the embodiments described herein.

In another aspect of the invention, the manipulator is configured to move such that an intermediate portion of the instrument shaft pivots about a remote center. Between the manipulator and the instrument, there are a plurality of driven joints providing sufficient degrees of freedom to allow a range of joint states for an end effector position when the intermediate portion of the instrument shaft passes through an access site. A processor having a controller couples the input device to the manipulator. In response to a reconfiguration command, the processor determines movements of one or more joints to effect the desired reconfiguration so that the intermediate portion of the instrument is within the access site during the end effector's desired movement and maintains the desired remote center location about which the shaft pivots. Typically, in response to receiving a manipulation command to effect a desired end effector's movement, the system calculates end effector displacing movement of the joints, comprising calculating joint velocities within a null-perpendicular-space of the Jacobian orthogonal to the null-space, and drives the joints according to the calculated movement to effect the desired end effector movement in which the instrument shaft pivots about the remote center.

In some embodiments, the manipulator includes a revolute joint coupling the manipulator arm to the base. The desired state of the end effector may include a desired position, velocity or acceleration of the end effector. The manipulation command and the reconfiguration command may be separate inputs, typically being received from separate users on separate input devices, or may be separate inputs are received from the same user. In some embodiments, the end effector manipulation command is received from an input device by a first user, such as a surgeon entering the command on a surgical console master input, while the reconfiguration command is received from an input device by a second user on a separate input device, such as a physician's assistant entering the reconfiguration command on a patient side cart input device. In other embodiments, the end effector manipulation command and the reconfiguration command are both received by the same user from input devices at a surgical console.

In yet another aspect of the present invention, a surgical robotic manipulator with a proximal revolute joint and a distal parallelogram linkage is provided, the pivotal axis of the revolute joint substantially intersecting with the axis of the instrument shaft of the end effector, preferably at a remote center if applicable. The system further includes a processor having a controller coupling the input to the manipulator arm and configured to calculate a movement of the plurality of joints in response to a user input command. The system may include an input device for receiving a reconfiguration command to move a first set of joints of the plurality of joints with a desired reconfiguration movement within the null-space or may include a clutch mode that allows a user to manually reconfigure one or more joints of the manipulator arm within the null-space as to maintain the end effector the desired state. The system may be configured to adjust or translate the positional constraints in response to a user driven reconfiguration or a manual reconfiguration of the manipulator arm, such as in a clutch mode, to allow for improved consistency and predictability of one or more joints within the null-space, while maintaining the desired state of the end effector, while providing the additional capability of a user input or manual reconfiguration.

A further understanding of the nature and advantages of the present invention will become apparent by reference to the remaining portions of the specification and drawings. It is to be understood, however, that each of the figures is provided for the purpose of illustration only and is not intended as a definition of the limits of the scope of the invention. Furthermore, it is appreciated than any of the features in any of the described embodiments could be modified and combined with any of various other features described herein or known to one of skill in the art and still remain within the spirit and scope of the invention.

BRIEF DESCRIPTION OF THE DRAWINGS

FIGS. 6A-6B show an exemplary manipulator arm in the pitch forward configuration and pitch back configurations, respectively.

FIG. 6C shows a graphical representation of the range of motion of the surgical instrument tool tip of an exemplary manipulator arm, including a cone of silence or conical tool access limit zone in each of the pitch forward and pitch back configurations.

DETAILED DESCRIPTION OF THE INVENTION

Figure 1A:
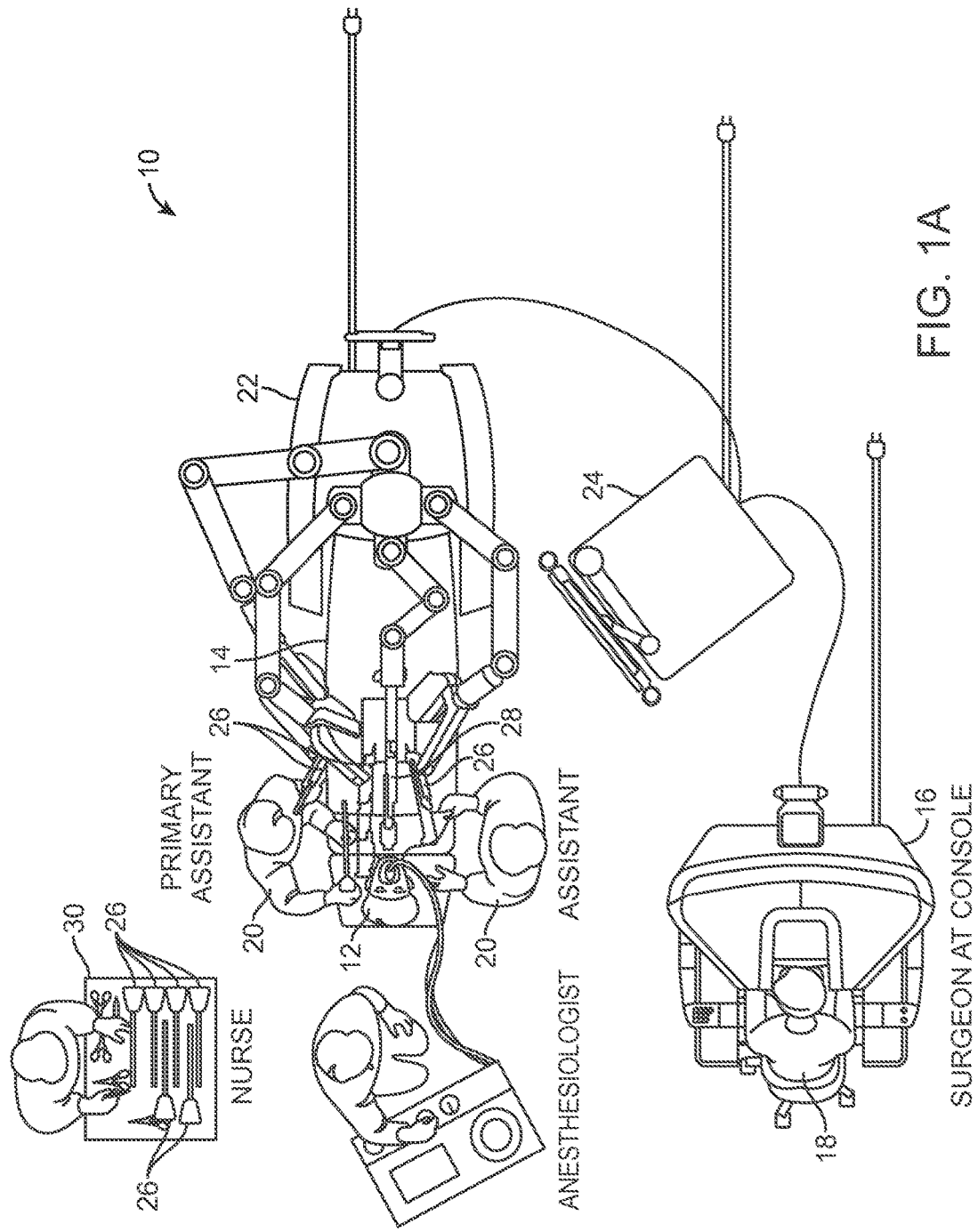
FIG. 1A is an overhead view of a robotic surgical system in accordance with embodiments of the present invention, the robotic surgical system having a surgical station with a plurality of robotic manipulators for robotically moving surgical instruments having surgical end effectors at an internal surgical site within a patient.

The present invention generally provides improved surgical and robotic devices, systems, and methods. The invention is particularly advantageous for use with surgical robotic systems in which a plurality of surgical tools or instruments may be mounted on and moved by an associated plurality of robotic manipulators during a surgical procedure. The robotic systems will often comprise telerobotic, telesurgical, and/or telepresence systems that include processors configured as master-slave controllers. By providing robotic systems employing processors appropriately configured to move manipulator assemblies with articulated linkages having relatively large numbers of degrees of freedom, the motion of the linkages can be tailored for work through a minimally invasive access site. The large number of degrees of freedom allows a system operator, or an assistant, to reconfigure the linkages of the manipulator assemblies while maintaining the desired end effector state, optionally in preparation for surgery and/or while another use maneuvers the end effector during a surgical procedure. While aspects of the invention are generally described manipulators having redundant degrees of freedom, it is appreciated that aspects may apply to non-redundant manipulators, for example a manipulator experiencing or approaching a singularity.

The robotic manipulator assemblies described herein will often include a robotic manipulator and a tool mounted thereon (the tool often comprising a surgical instrument in surgical versions), although the term "robotic assembly" will also encompass the manipulator without the tool mounted thereon. The term "tool" encompasses both general or industrial robotic tools and specialized robotic surgical instruments, with these later structures often including an end effector which is suitable for manipulation of tissue, treatment of tissue, imaging of tissue, or the like. The tool/manipulator interface will often be a quick disconnect tool holder or coupling, allowing rapid removal and replacement of the tool with an alternate tool. The manipulator assembly will often have a base which is fixed in space during at least a portion of a robotic procedure, and the manipulator assembly may include a number of degrees of freedom between the base and an end effector of the tool. Actuation of the end effector (such as opening or closing of the jaws of a gripping device, energizing an electrosurgical paddle, or the like) will often be separate from, and in addition to, these manipulator assembly degrees of freedom.

The end effector will typically move in the workspace with between two and six degrees of freedom. As used herein, the term "position" encompasses both location and orientation. Hence, a change in a position of an end effector (for example) may involve a translation of the end effector from a first location to a second location, a rotation of the end effector from a first orientation to a second orientation, or a combination of both. When used for minimally invasive robotic surgery, movement of the manipulator assembly may be controlled by a processor of the system so that a shaft or intermediate portion of the tool or instrument is constrained to a safe motion through a minimally invasive surgical access site or other aperture. Such motion may include, for example, axial insertion of the shaft through the aperture site into a surgical workspace, rotation of the shaft about its axis, and pivotal motion of the shaft about a pivot point adjacent the access site.

Many of the exemplary manipulator assemblies described herein have more degrees of freedom than are needed to position and move an end effector within a surgical site. For example, a surgical end effector that can be positioned with six degrees of freedom at an internal surgical site through a minimally invasive aperture and may in some embodiments have nine degrees of freedom (six end effector degrees of freedom-three for location, and three for orientation—plus three degrees of freedom to comply with the access site constraints), but will often have ten or more degrees of freedom. Highly configurable manipulator assemblies having more degrees of freedom than are needed for a given end effector position can be described as having or providing sufficient degrees of freedom to allow a range of joint states for an end effector position in a workspace. For example, for a given end effector position, the manipulator assembly may occupy (and be driven between) any of a range of alternative manipulator linkage positions. Similarly, for a given end effector velocity vector, the manipulator assembly may have a range of differing joint movement speeds for the various joints of the manipulator assembly within the null-space of the Jacobian.

The invention provides robotic linkage structures which are particularly well suited for surgical (and other) applications in which a wide range of motion is desired, and for which a limited dedicated volume is available due to the presence of other robotic linkages, surgical personnel and equipment, and the like. The large range of motion and reduced volume needed for each robotic linkage may also provide greater flexibility between the location of the robotic support structure and the surgical or other workspace, thereby facilitating and speeding up setup.

The term "state" of a joint or the like will often herein refer to the control variables associated with the joint. For example, the state of an angular joint can refer to the angle defined by that joint within its range of motion, and/or to the angular velocity of the joint. Similarly, the state of an axial or prismatic joint may refer to the joint's axial position, and/or to its axial velocity. While many of the controllers described herein comprise velocity controllers, such controllers may also include some position control aspects. Alternative embodiments may rely primarily or entirely on position controllers, acceleration controllers, or the like. Many aspects of control system that can be used in such devices are more fully described in U.S. Pat. No. 6,699,177, the full disclosure of which is incorporated herein by reference. Hence, so long as the movements described are based on the associated calculations, the calculations of movements of the joints and movements of an end effector described herein may be performed using a position control algorithm, a velocity control algorithm, a combination of both, and/or the like.

In one aspect, the tool of an exemplary manipulator arm pivots about a pivot point adjacent a minimally invasive aperture. The system may utilize a hardware remote center, such as the remote center kinematics described in U.S. Pat. No. 6,786,896, the entire contents of which are incorporated herein in its entirety. Such systems may utilize a double parallelogram linkage which constrains the movement of the linkages such that the shaft of the instrument supported by the manipulator pivots about a remote center point. Alternative mechanically constrained remote center linkage systems are known and/or may be developed in the future. Surprisingly, work in connection with various aspects of the invention indicates that remote center linkage systems may benefit substantially from highly configurable kinematic architectures. In particular, when a surgical robotic system has a linkage that allows pivotal motion about two axes intersecting at or near a minimally invasive surgical access site, the spherical pivotal motion may encompass the full extent of a desired range of motion within the patient, but may still suffer from avoidable deficiencies, such as being poorly conditioned, being susceptible to arm-to-arm or arm-to-patient contact outside the patient, and/or the like. At first, adding one or more additional degrees of freedom that are also mechanically constrained to pivotal motion at or near the access site may appear to offer few or any improvements in the range of motion. Nonetheless, such joints can provide significant advantages by allowing the overall system to be configured in or driven toward a collision-inhibiting pose, by further extending the range of motion for other surgical procedures, and the like.

In another aspect, the system may utilize software to achieve a remote center, such as described in U.S. Pat. No. 8,004,229, the entire contents of which are incorporated herein by reference. In a system having a software remote center, the processor calculates movement of the joints so as to pivot an intermediate portion of the instrument shaft about a pivot point determined, as opposed to a mechanical constraint. By having the capability to compute software pivot points, different modes characterized by the compliance or stiffness of the system can be selectively implemented. More particularly, different system modes over a range of pivot points/centers (e.g., moveable pivot points, passive pivot points, fixed/rigid pivot point, soft pivot points) can be implemented as desired.

Despite the many advantages of a robotic surgical system having multiple highly configurable manipulators, since the manipulators include a relatively large number of joints and links between the base and instrument, manual positioning of the links can be challenging and complicated. Even when the manipulator structure is balanced so as to avoid gravitational effects, attempting to align each of the joints in an appropriate arrangement or to reconfigure the manipulator as desired can be difficult, time consuming, and may involve significant training and/or skill. The challenges can be even greater when the links of the manipulator are not balanced about the joints, such that positioning such a highly configurable structures in an appropriate configuration before or during surgery can be a struggle due to the manipulator arm length and the passive and limp design in many surgical systems.

These issues can be addressed by allowing a user, such as a physician's assistant, to quickly and easily reconfigure the manipulator arm, while and maintaining the desired end effector state, optionally even during movement of the end effector during a surgical procedure. One or more additional joints may be included in the manipulator arm to increase the range of motion and configurations of the manipulator arm to enhance this capability. While providing additional joints may provide increased range of motion for certain tasks, various combinations of joint states may unnecessarily limit the available range of joint movement, particularly near the joint limits of one or more joints of the manipulator.

In some embodiments, calculated movement relating to various other tasks, such as an avoidance movement based on an autonomous algorithm, may overlay the access facilitating movement so that the one or more joints may be moved to effect various other tasks, as needed. Examples of such avoidance movement are described in U.S. Provisional Application No. 61/654,755 filed Jun. 1, 2012, entitled "Manipulator Arm-to-Patient Collision Avoidance Using a Null-Space;" and U.S. Provisional Application No. 61/654,773 filed Jun. 1, 2012, entitled "System and Methods for Avoiding Collisions Between Manipulator Arms Using a Null-Space," the disclosures of which are incorporated herein by reference in their entireties. The calculated movement that overlays the facilitating movement of the one or more joints, however, is not limited to the autonomous movement and may include various other movements, such as a commanded reconfiguration movement or various other movements.

Embodiments of the invention may include a user input which is configured to take advantage of the degrees of freedom of a manipulator structure. Rather than manually reconfiguring the manipulator, the input facilitates use of driven joints of the kinematic linkage to reconfigure the manipulator structure in response to entry of a reconfiguration command by a user. The user input for receiving the reconfiguration command may be incorporated into and/or disposed near the manipulator arm. In some embodiments, the input comprises a centralized input device to facilitate reconfiguration of one or more joints, such as a cluster of buttons on the patient side cart or a joystick. Typically, the input device for receiving the reconfiguration command is separate from the input for receiving a manipulation command to effect movement of the end effector. A controller of the surgical system may include a processor with readable memory having joint controller programming instructions or code recorded thereon which allows the processor to derive suitable joint commands for driving the joints recorded thereon so as to allow the controller to effect the desired reconfiguration in response to entry of the reconfiguration command. It is appreciated, however, that the invention may be used in a manipulator arm with or without a reconfiguration feature.

In the following description, various embodiments of the present invention will be described. For purposes of explanation, specific configurations and details are set forth in order to provide a more thorough understanding of the embodiments. However, it will also be apparent to one skilled in the art that the present invention may be practiced without various specific details. Furthermore, well-known features may be omitted or simplified in order not to obscure the embodiment being described.

Referring now to the drawings, in which like reference numerals represent like parts throughout the several views, FIG. 1A is an overhead view illustration of a Minimally Invasive Robotic Surgical (MIRS) system 10, in accordance with many embodiments, for use in performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 so as to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 1B:
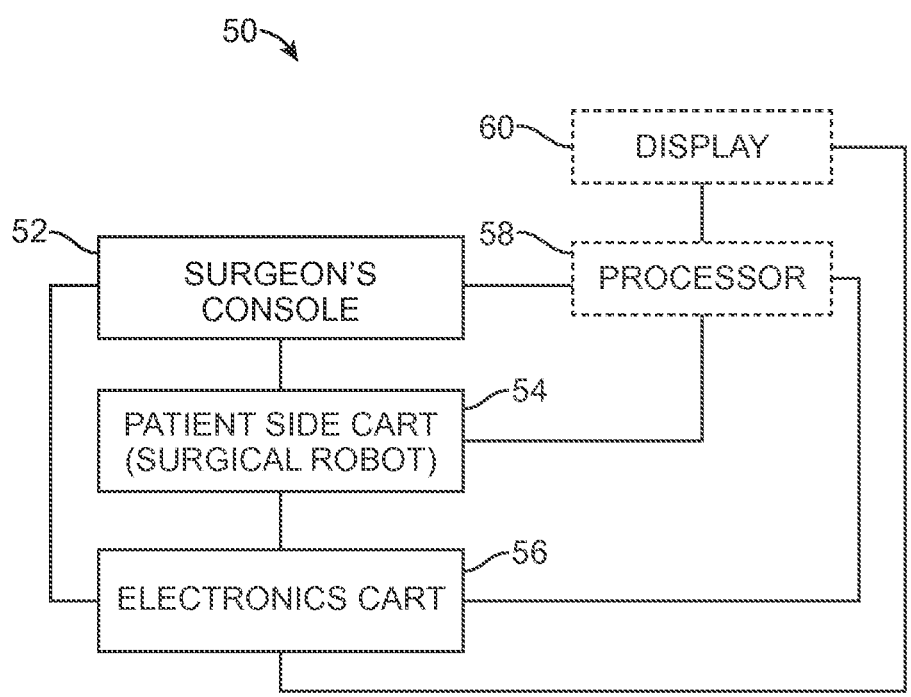
FIG. 1B diagrammatically illustrates the robotic surgical system of FIG. 1A.

FIG. 1B diagrammatically illustrates a robotic surgery system 50 (such as MIRS system 10 of FIG. 1A). As discussed above, a Surgeon's Console 52 (such as Surgeon's Console 16 in FIG. 1A) can be used by a Surgeon to control a Patient Side Cart (Surgical Robot) 54 (such as Patent Side Cart 22 in FIG. 1A) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1A). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together so as to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 2:
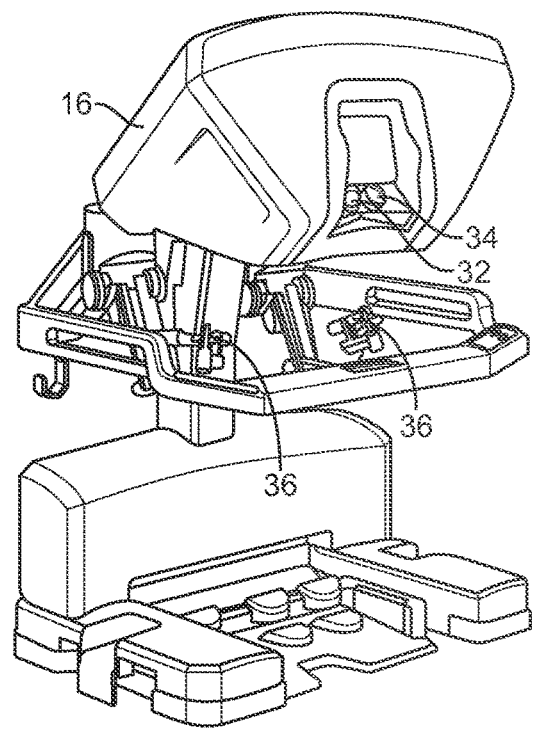
FIG. 2 is a perspective view illustrating a master surgeon console or workstation for inputting surgical procedure commands in the surgical system of FIG. 1A, the console including a processor for generating manipulator command signals in response to the input commands.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1A) to manipulate one or more tools. The input control devices 36 can provide the same degrees of freedom as their associated tools 26 (shown in FIG. 1A) so as to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
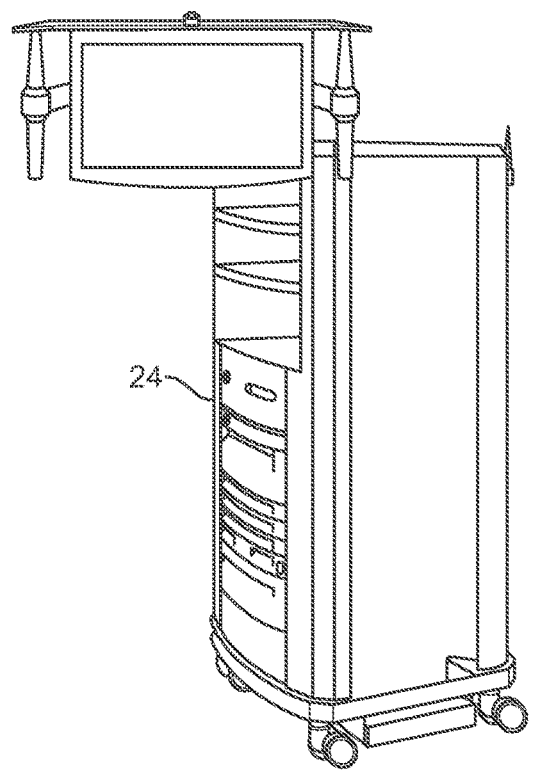
FIG. 3 is a perspective view of the electronics cart of FIG. 1A.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images so as to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters so as to compensate for imaging errors of the image capture device, such as optical aberrations.

Figure 4:
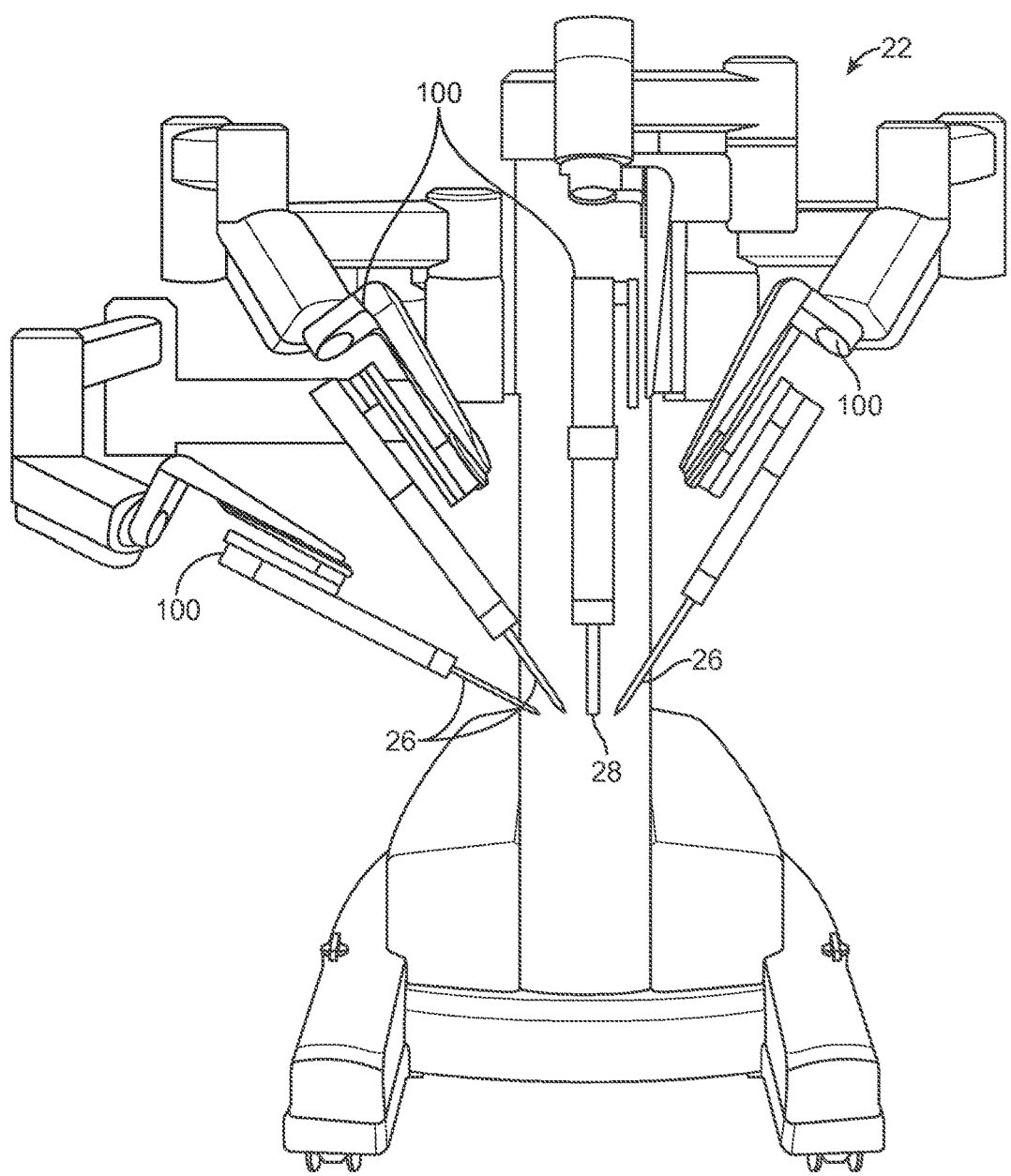
FIG. 4 is a perspective view of a patient side cart having four manipulator arms.

FIG. 4 shows a Patient Side Cart 22 having a plurality of manipulator arms, each supporting a surgical instrument or tool 26 at a distal end of the manipulator arm. The Patient Side Cart 22 shown includes four manipulator arms 100 which can be used to support either a surgical tool 26 or an imaging device 28, such as a stereoscopic endoscope used for the capture of images of the site of the procedure. Manipulation is provided by the robotic manipulator arms 100 having a number of robotic joints. The imaging device 28 and the surgical tools 26 can be positioned and manipulated through incisions in the patient so that a kinematic remote center is maintained at the incision so as to minimize the size of the incision. Images of the surgical site can include images of the distal ends of the surgical instruments or tools 26 when they are positioned within the field-of-view of the imaging device 28.

Regarding surgical tool 26, a variety of alternative robotic surgical tools or instruments of different types and differing end effectors may be used, with the instruments of at least some of the manipulators being removed and replaced during a surgical procedure. Several of these end effectors, including DeBakey Forceps, microforceps, Potts scissors, and clip applier include first and second end effector elements which pivot relative to each other so as to define a pair of end effector jaws. Other end effectors, including scalpel and electrocautery probe have a single end effector element. For instruments having end effector jaws, the jaws will often be actuated by squeezing the grip members of handle. Single end effector instruments may also be actuated by gripping of the grip members, for example, so as to energize an electrocautery probe.

The elongate shaft of instrument 26 allow the end effectors and the distal end of the shaft to be inserted distally into a surgical worksite through a minimally invasive aperture, often through an abdominal wall or the like. The surgical worksite may be insufflated, and movement of the end effectors within the patient will often be effected, at least in part, by pivoting of the instrument 26 about the location at which the shaft passes through the minimally invasive aperture. In other words, manipulators 100 will move the proximal housing of the instrument outside the patient so that shaft extends through a minimally invasive aperture location so as to help provide a desired movement of end effector. Hence, manipulators 100 will often undergo significant movement outside patient P during a surgical procedure.

Exemplary manipulator arms in accordance with many embodiments of the present invention can be understood with reference to FIGS. 5A-12C. As described above, a manipulator arm generally supports a distal instrument or surgical tool and effects movements of the instrument relative to a base. As a number of different instruments having differing end effectors may be sequentially mounted on each manipulator during a surgical procedure (typically with the help of a surgical assistant), a distal instrument holder will preferably allow rapid removal and replacement of the mounted instrument or tool. As can be understood with reference to FIG. 4, manipulators are proximally mounted to a base of the patient side cart. Typically, the manipulator arm includes a plurality of linkages and associated joints extending between the base and the distal instrument holder. In one aspect, an exemplary manipulator includes a plurality of joints having redundant degrees of freedom such that the joints of the manipulator arm can be driven into a range of differing configurations for a given end effector position. This may be the case for any of the embodiments of manipulator arms disclosed herein.

Figure 5A:
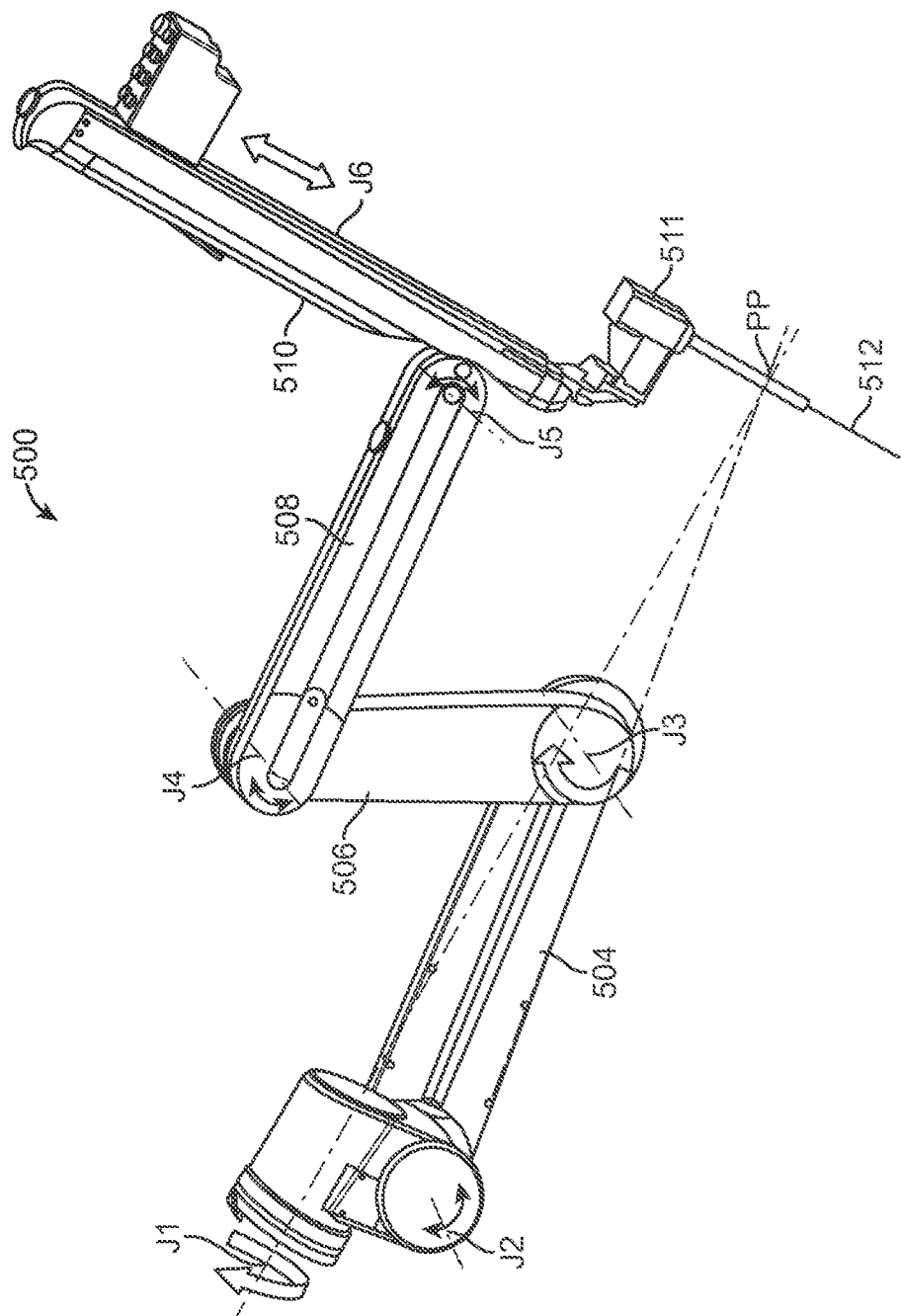
FIGS. 5A-5D show an exemplary manipulator arm.

In many embodiments, such as the example in FIG. 5A, the manipulator arm includes a proximal revolute joint J1 that rotates about a first joint axis so as to revolve the manipulator arm distal of the joint about the joint axis. Revolute joint J1 is mounted directly to the base or may be mounted to one or more movable linkages or joints. The joints of the manipulator, in combination, have redundant degrees of freedom such that the joints of the manipulator arm can be driven into a range of differing configurations for a given end effector position. For example, the manipulator arm of FIGS. 5A-5D may be maneuvered into differing configurations while the distal member 511 (such as a cannula through which the tool 512 or instrument shaft extends) supported within the instrument holder 510 maintains a particular state and may include a given position or velocity of the end effector. Distal member 511 is typically a cannula through which the tool shaft 512 extends, and the instrument holder 510 is typically a carriage (shown as a brick-like structure that translates on a spar) to which the instrument attaches before extending through the cannula 511 into the body of the patient through the minimally invasive aperture.

Figure 5B:
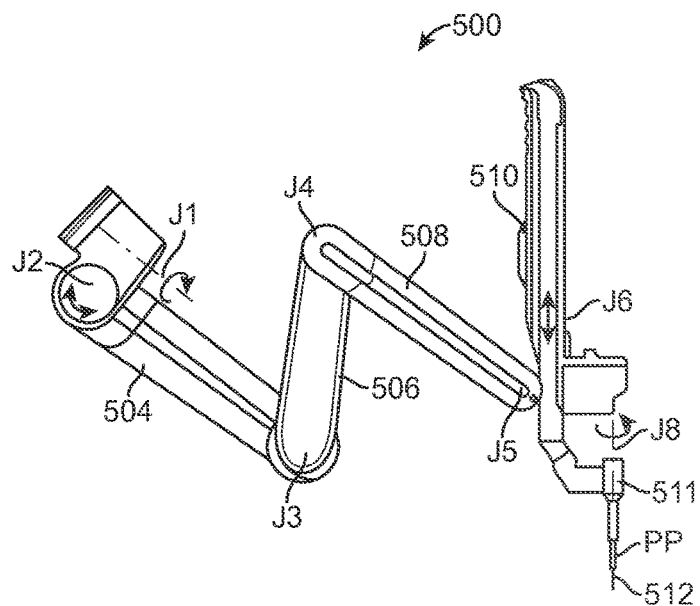
Figure 5D:
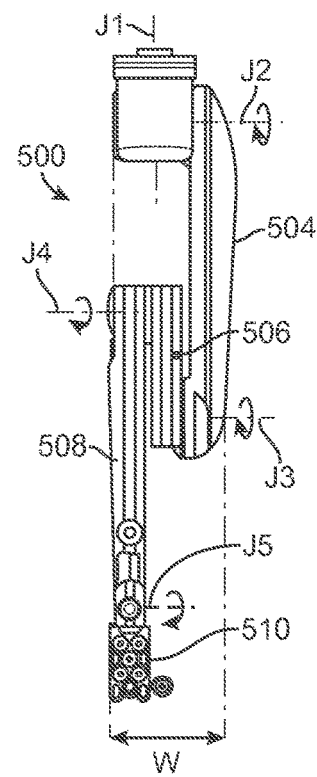
Figure 5C:
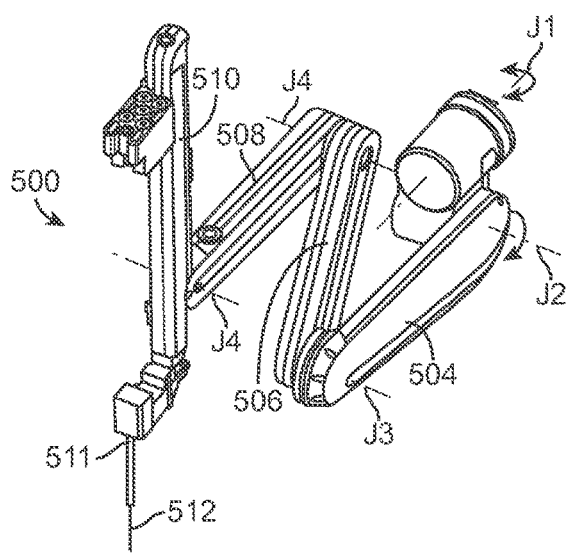

Describing the individual links of the example manipulator arm 500 of FIGS. 5A-5D along with the axes of rotation of the joints connecting the links as illustrated in FIG. 5A-5D, a first link 504 extends distally from a pivotal joint J2 which pivots about its joint axis and is coupled to revolute joint J1 which rotates about its joint axis. Many of the remainder of the joints can be identified by their associated rotational axes, as shown in FIG. 5A. For example, a distal end of first link 504 is coupled to a proximal end of a second link 506 at a pivotal joint J3 that pivots about its pivotal axis, and a proximal end of a third link 508 is coupled to the distal end of the second link 506 at a pivotal joint J4 that pivots about its axis, as shown. The distal end of the third link 508 is coupled to instrument holder 510 at pivotal joint J5. Typically, the pivotal axes of each of joints J2, J3, J4, and J5 are substantially parallel and the linkages appear "stacked" when positioned next to one another, as shown in FIG. 5D, so as to provide a reduced width w of the manipulator arm and improve patient clearance during maneuvering of the manipulator assembly. In certain embodiments, the instrument holder includes additional joints, such as a prismatic joint J6 that facilitates axial movement of instrument 306 through the minimally invasive aperture and facilitates attachment of the instrument holder to a cannula through which the instrument is slidably inserted.

In this example manipulator arm, the distal member or cannula 511 through which the tool 512 extends may include additional degrees of freedom distal of instrument holder 510. Actuation of the degrees of freedom of the instrument will often be driven by motors of the manipulator, and alternative embodiments may separate the instrument from the supporting manipulator structure at a quickly detachable instrument holder/instrument interface so that one or more joints shown here as being on the instrument are instead on the interface, or vice versa. In some embodiments, cannula 511 includes a rotational joint J8 (not shown) near or proximal of the insertion point of the tool tip or the pivot point PP, which generally is disposed at the site of a minimally invasive aperture. A distal wrist of the instrument allows pivotal motion of an end effector of surgical tool 512 about instrument joints axes of one or more joints at the instrument wrist. An angle between end effector jaw elements may be controlled independently of the end effector location and orientation.

The range of motion of an example manipulator assembly can be appreciated by referring to the examples in FIGS. 6A-6C. During a surgical procedure, the manipulator arm can be maneuvered into a pitch forward configuration, as shown in FIG. 6A, or into a pitch back configuration, as shown in FIG. 6B, as needed to access particular patient tissues within a surgical workspace. A typical manipulator assembly includes an end effector that can pitch forwards and backwards about an axis by at least ±60 degrees, preferably by about ±75 degrees, and can also yaw about an axis by ±80 degrees. Although this aspect allows for increased maneuverability of the end effector with the assembly, there may be configurations in which movement of the end effector may be limited, particularly when the manipulator arm is in the full pitch forward or full pitch back configuration as in FIGS. 6A and 6B. In this embodiment, the manipulator arm has a Range of Motion (ROM) of (±75 deg) for the outer pitch, and (±300 degrees) for the outer yaw joints, respectively. In some embodiments, the ROM may be increased for the outer pitch to provide a ROM larger than (±90 deg) in which case the "cone of silence" could be made to disappear entirely, although generally the inner sphere associated with insertion limitations would remain. It is appreciated the manipulator may be configured to have increased or decreased ROM, that the above noted ROMs are provided for illustrative purposed, and further that the invention is not limited to the ROMs described herein.

FIG. 6C graphically represents the overall range of motion and workspace of the tool tip of the exemplary manipulator of FIGS. 5A-5B. Although the workspace is shown as hemisphere, it may also be represented as a sphere depending on the range of motion and configuration of one or more revolute joints of the manipulator, such as joint J1. As shown, the hemisphere in FIG. 6C includes a central, small spherical void as well as two conical voids. The voids represent the areas in which movement of the tool tip may be impossible due to mechanical constraints or unfeasible due to extremely high joint velocities that make movement of the end effector difficult or slow. For these reasons, the conical void are referred to as the "cone of silence." In some embodiments, the manipulator arm may reach a singularity at a point within the cone. Since movement of the manipulator within or near the cone of silence may be impaired, it can be difficult to move the manipulator arm away from the cone of silence without manually moving one or more links of the manipulator to reconfigure the linkages and joints of the manipulator, which often requires an alternative operating mode and delays the surgical procedure.

Movement of the instrument shaft into or near these conical portions typically occurs when the angle between distal linkages in the manipulator is relatively small. Such configurations can be avoided by reconfiguring the manipulator to increase the angles between linkages (so that the linkages are moved into a more orthogonal position relative to each other). For example, in the configurations shown in FIGS. 6A and 6B, when the angle between the distal most link and the instrument holder (angle α) becomes relatively small, movement of the manipulator becomes more difficult. Depending on the range of joint movements in the remaining joints in various embodiments, when the angle between certain linkages decreases, movement of the manipulator may be inhibited and in some cases, the manipulator arm may no longer be redundant. A manipulator configuration in which the instrument shaft nears these conical portions, or in which the angles between linkages are relatively low is said to be "poorly conditioned" such that maneuverability and dexterity of the manipulator arm is limited. It is desirable that the manipulator be "well conditioned" so as to maintain dexterity and range of movement. In one aspect, the present invention allows a user to avoid movement of the instrument shaft near the above described conical portions by simply entering a command to reconfigure the manipulator as desired, even during movement of the end effector in a surgical procedure. This aspect is particularly useful should the manipulator, for whatever reason, become "poorly conditioned."

While the embodiments described are utilized in the present invention, some embodiments may include additional joints, which may also be used to improve dexterity and the conditioning of the manipulator arm. For example, an exemplary manipulator may include a revolute joint and/or linkage proximal of joint J1 which can be used to revolve the manipulator arm of FIG. 5A, and its associated cone of silence, about an axis of the revolute joint so as to reduce or eliminate the cone of silence. In another embodiment, the exemplary manipulator may also include a distal pivotal joint that pivots the instrument holder about an axis substantially perpendicular to joint J5, thereby offsetting the tool tip so as to further reduce the cone of silence and improve the range of movement of the surgical tool. In still another embodiment, a proximal joint of the manipulator arm, such as J1, may be movably mounted on the base, so as to move or shift the cone of silence as needed and improve the range of motion of the manipulator tool tip. The use and advantages of such additional joints can be understood by referring to FIGS. 7A-12C, which illustrate examples of such joints, which may each be used independent of one another or used in combination, in any of the exemplary manipulator arms described herein.

Figure 7A:
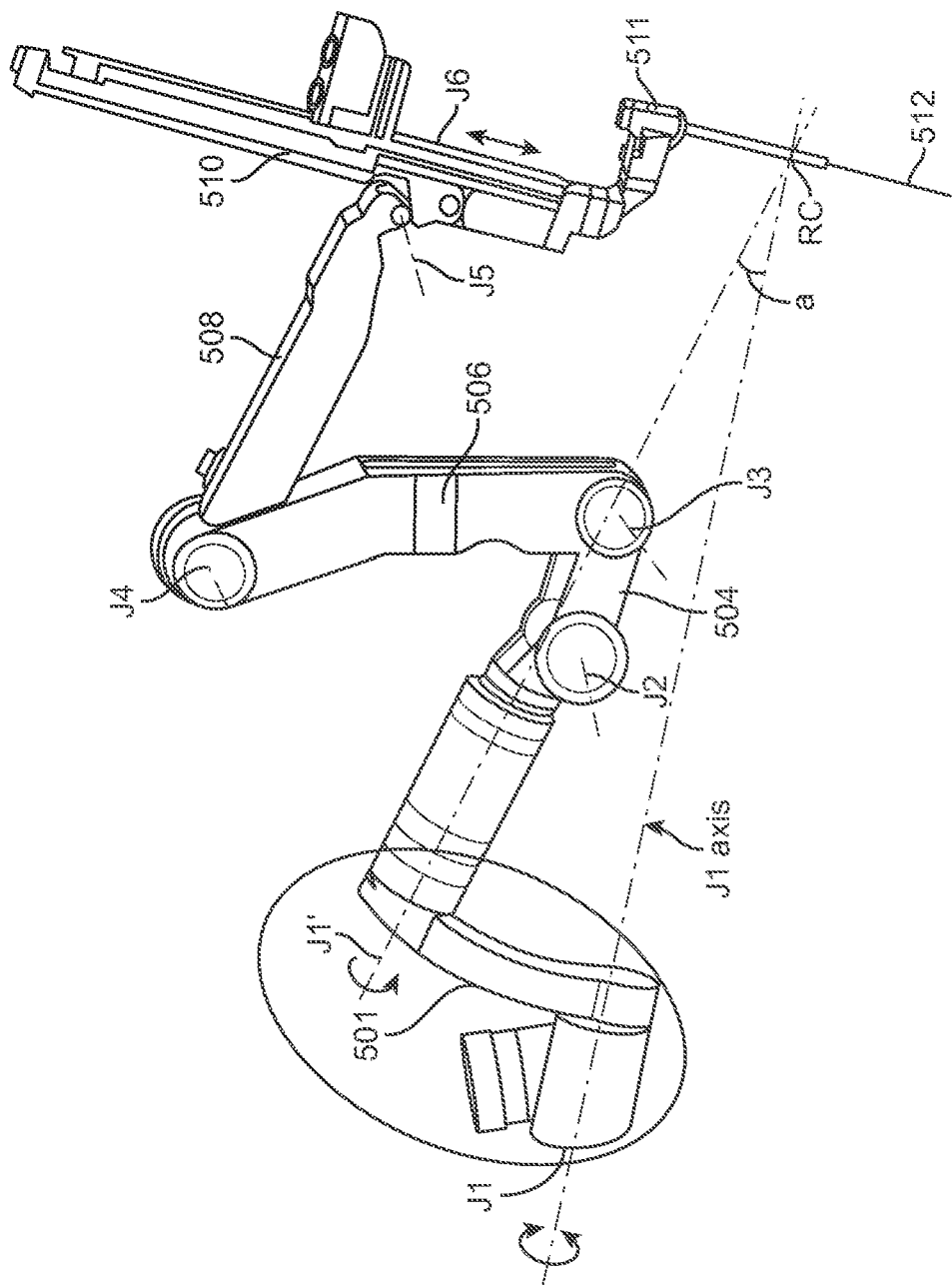
FIG. 7A shows exemplary manipulator arms having a proximal revolute joint that revolves the manipulator arm about an axis of a proximal revolute joint.
Figure 7B:
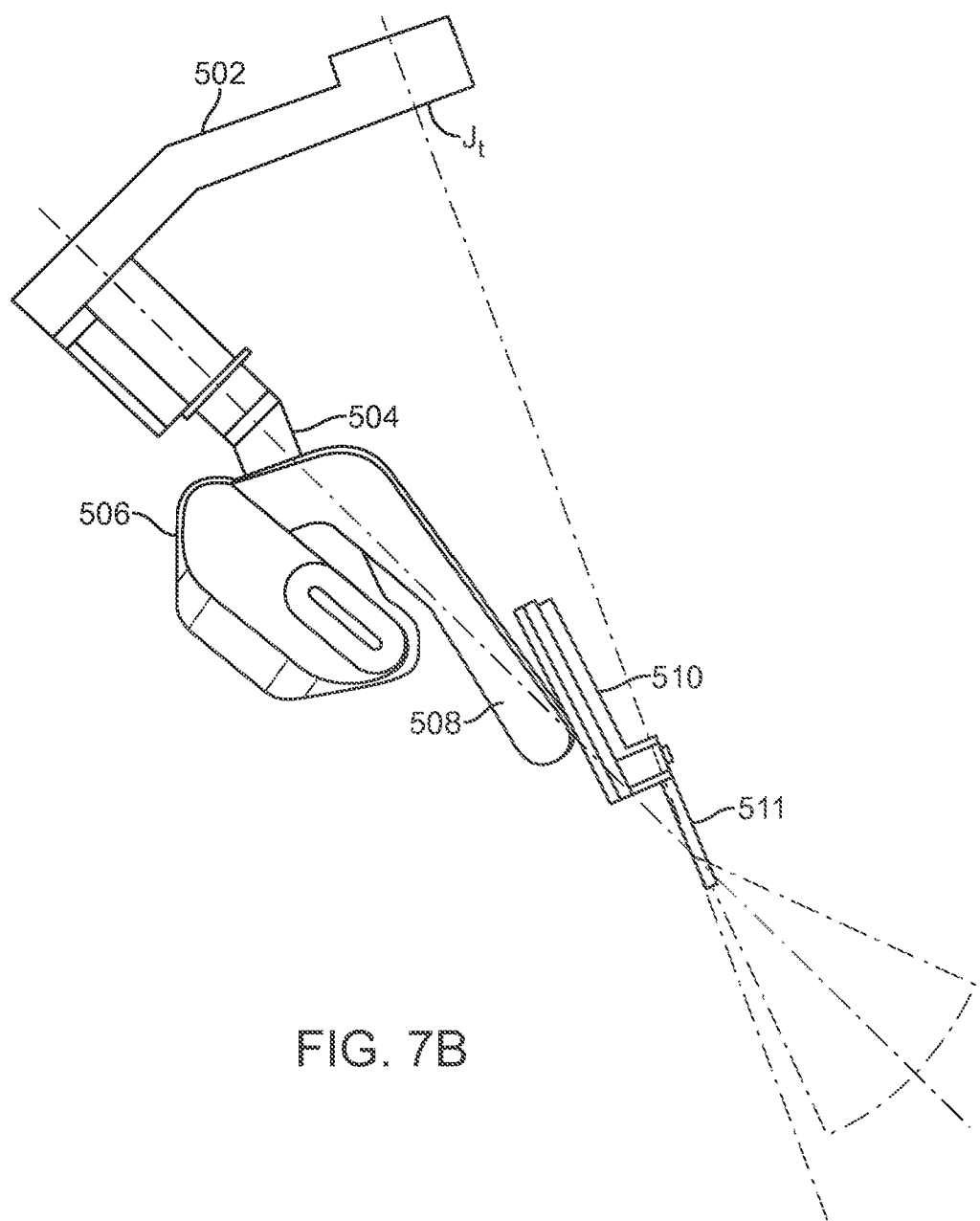
FIG. 7B shows an exemplary manipulator arm and the associated range of motion and cone of silence, the exemplary manipulator arm having a proximal revolute joint that revolves the manipulator arm around an axis of a proximal revolute joint the movement of which can be used to mitigate the depicted cone of silence.

FIGS. 7A-7B illustrate an additional redundant joint for use with exemplary manipulator arms—a first joint coupling a proximal portion of the manipulator arm to the base. The first joint is a proximal revolute joint J1' that revolves the manipulator arm about a joint axis of joint J1'. The proximal revolute J1' includes a link 501 that offsets joint J1 from the proximal revolute J1' by a pre-determined distance or angle. The link 501 can be a curved linkage, as shown in FIG. 7A, or a linear or angled linkage, as shown in FIG. 7B. Typically, the joint axis of the joint J1' is aligned with the remote center RC or insertion point of the tool tip, as shown in each of FIG. 7A. In an exemplary embodiment, the joint axis of joint J1' passes through the remote center, as does each other revolute joint axis in the manipulator arm, to prevent motion at the body wall and can therefore be moved during surgery. The axis of joint J1' is coupled to a proximal portion of the arm so it can be used to change the position and orientation of the back of the arm. In general, redundant axes, such as this, allow the instrument tip to follow the surgeon's commands while simultaneously avoiding collisions with other arms or patient anatomy. In one aspect, the proximal revolute J1' is used solely to change the mounting angle of the manipulator with respect to the floor. This angle is important in order to 1) avoid collisions with external patient anatomy and 2) reach anatomy inside the body. Typically, the angle α between the proximal link of the manipulator attached to the proximal revolute joint J1' and the axis of the proximal revolute is about 15 degrees.

FIG. 7B illustrates the relationship of the proximal revolute joint J1' and its associated joint axis and the cone of silence in an exemplary manipulator arm. The joint axis of the proximal revolute joint J1' may pass through the cone of silence or may be completely outside of the cone of silence. By revolving the manipulator arm about the axis of the proximal revolute J1', the cone of silence can be reduced (in an embodiment where the joint J1' axis passes through the cone of silence), or can be effectively eliminated (in an embodiment where the proximal revolute joint axis extends completely outside the cone of silence). The distance and angle of the link 501 determines the position of the joint J1' axis relative to the cone of silence.

Figure 8:
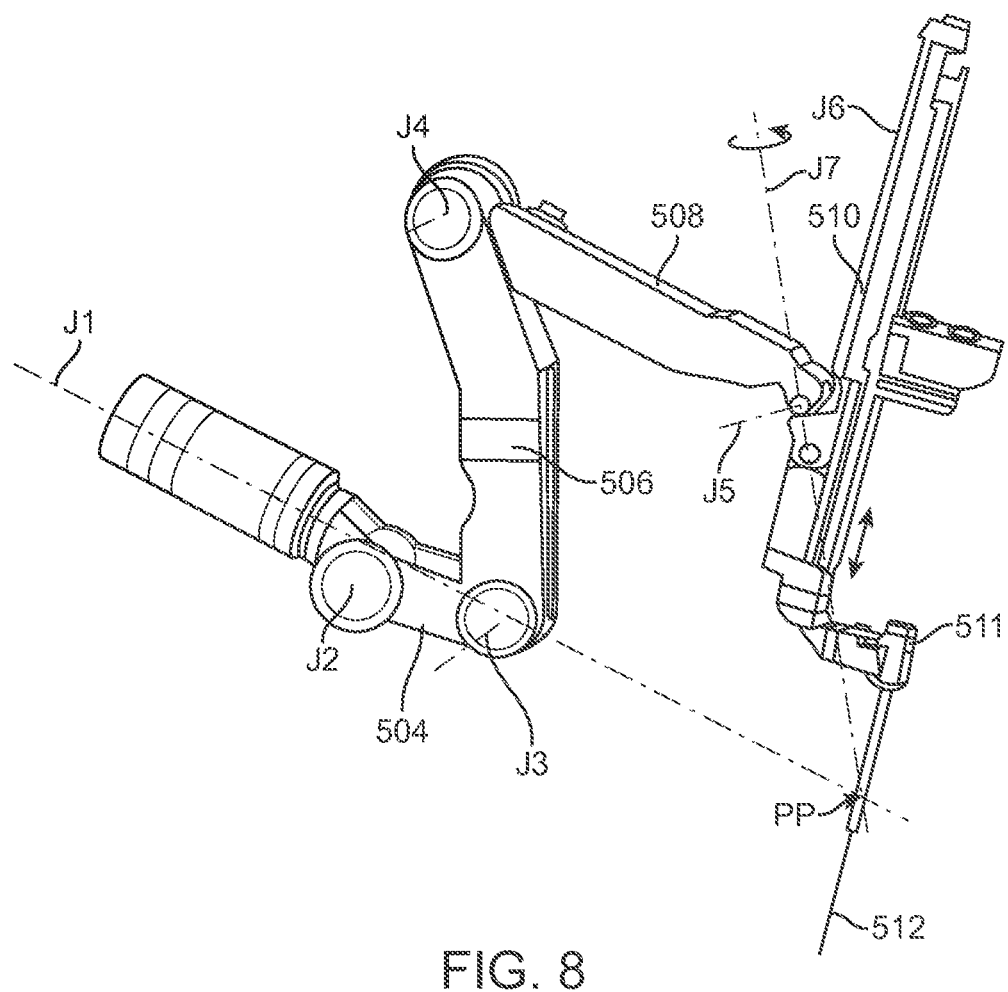
FIGS. 8 and 9 show an exemplary manipulator arms having a revolute joint near the distal instrument holder.
Figure 9:
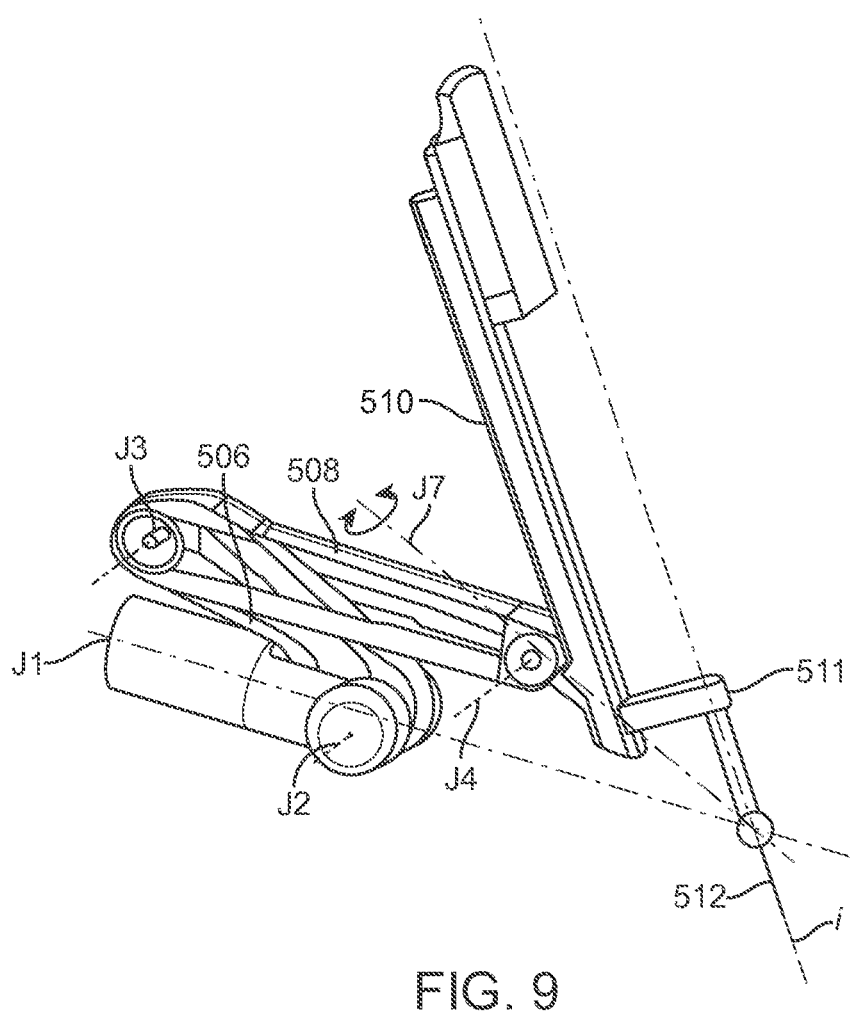
Figure 10A:
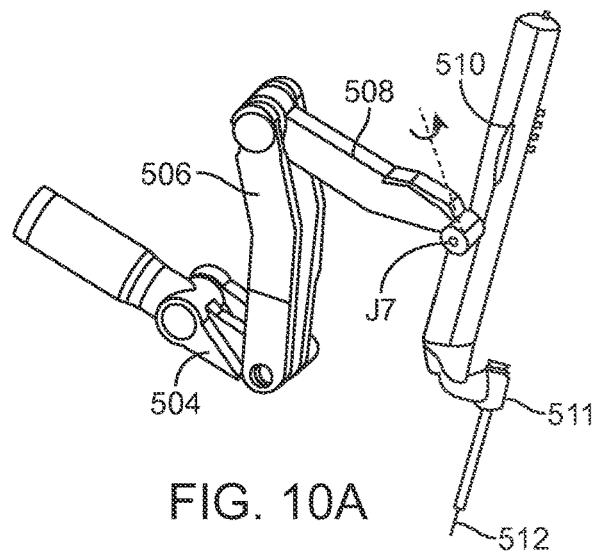
FIGS. 10A-10C show sequential views of an exemplary manipulator arm having a revolute joint near a distal instrument holder as the joint is moved throughout its range of joint movement.
Figure 10B:
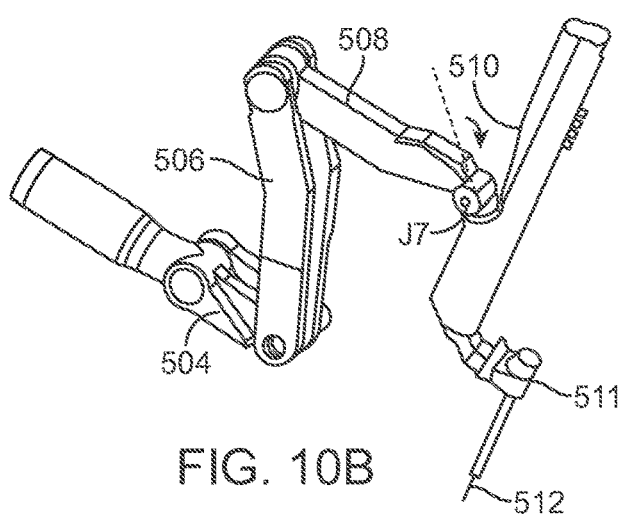
Figure 10C:
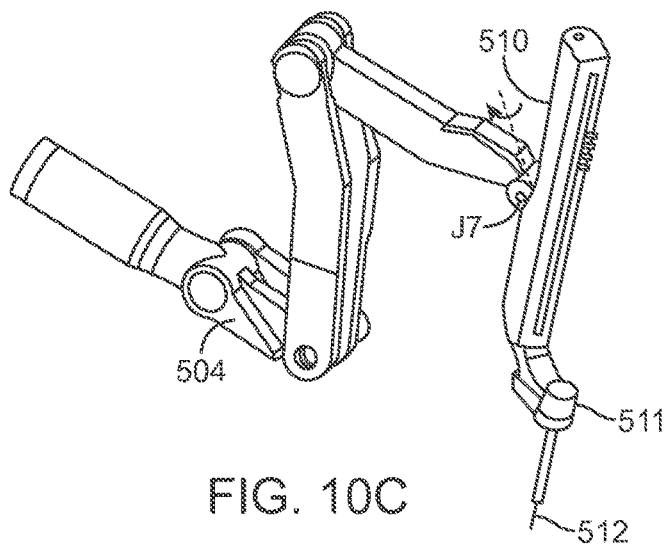

FIGS. 8-9 illustrates another type of redundant joint for use with exemplary manipulator arms, a distal revolute joint J7 coupling the instrument holder 510 to a distal link of the manipulator arm 508. The distal revolute joint J7 allows the system to laterally pivot or twist the instrument holder 510 about the joint axis, which typically passes through the remote center or insertion point. Ideally, the revolute joint is located distally on the arm and is therefore particularly well suited to moving the orientation of the insertion axis. The addition of this redundant axis allows the manipulator to assume multiple positions for any single instrument tip position. In general, redundant axes, such as this, allow the instrument tip to follow the surgeon's commands while simultaneously avoiding collisions with other arms or patient anatomy. Because the distal revolute joint J7 has the ability to move the insertion axis closer to the yaw axis, it is able to increase the range of motion when the manipulator arm is in a pitch back position. FIGS. 10A-10C show the sequential movement of joint J7 and how movement of joint J7 shifts the insertion axis of tool tip from side to side.

In another aspect, any of the systems described herein may utilize a user input device to drive one or more joints and reconfigure one or more joints of the manipulator arm within a null-space to effect a desired reconfiguration for a variety of reasons. In an embodiment having one or both of a user input for commanded reconfiguration or a mode as described above, the system may utilize the constraints described above during movement to effect commanded manipulation movement and suspend application of the constraints during a reconfiguration movement or while in the clutch mode. When the reconfiguration movement is completed or the manipulator arm is switched out of clutch mode, the system applies the position-based constraints according to the reconfigured location of the manipulator arm. In other embodiments, the constraints may define multiple positional paths of movement such that the constraints associated with the closest path within the Cartesian-coordinate space can be selected. These aspects allow the system to provide the desired movement of the one or more joints of the manipulator arm after being reconfigured, by a driven reconfiguration or a manual reconfiguration while in a clutch mode.

Figure 11A:
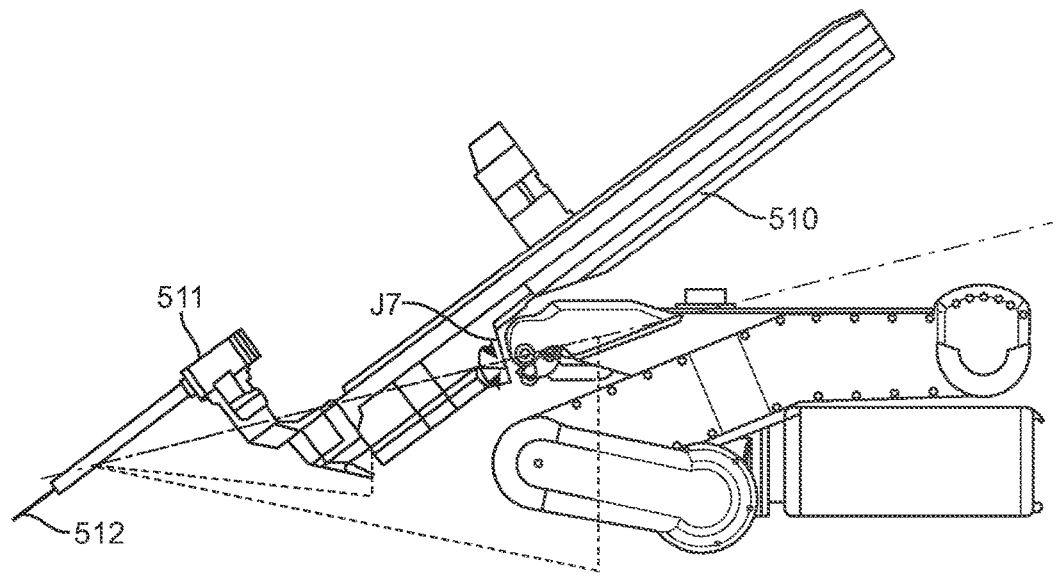
FIGS. 11A-11B show the revolved profile of an exemplary manipulator arm having a distal revolute joint when the angular displacement of the joint is 0° versus an angular displacement of 90°, respectively.
Figure 11B:
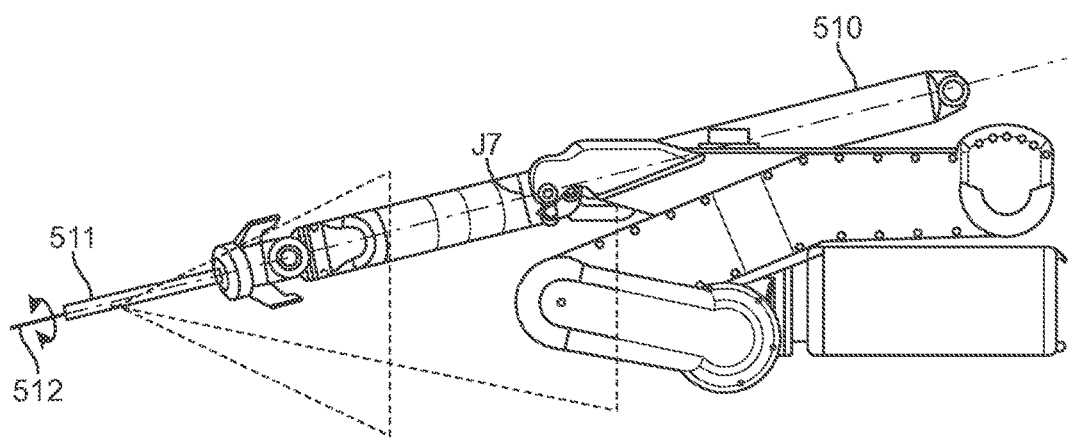

One advantage of using an additional redundant joint, such as distal revolute joint J7, is that it may be used to reduce the patient clearance cone, which is the swept volume of the distal portion of the manipulator arm proximal of the insertion point which must clear the patient to avoid collision between the patient and the instrument holder or distal linkages of the manipulator arm. FIG. 11A illustrates the patient clearance cone of the proximal portion of the manipulator arm while the angular displacement of the distal revolute joint remains at 0°. FIG. 11B illustrates the reduced patient clearance cone of the proximal portion of the manipulator arm while the distal revolute joint is shown having an angular displacement of 90° about its axis. Thus, in procedures having minimal patient clearance near the insertion point, use of the joint J7 in accordance with the present invention may provide additional clearance while maintaining the remote center location or the position of the end effector as desired.

Figure 12A:
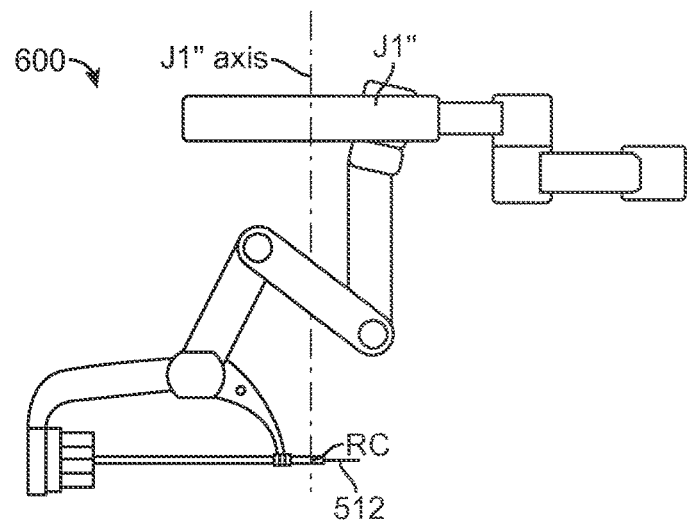
FIGS. 12A-12C show exemplary manipulator arms having a proximal joint that translates a proximal joint supporting the manipulator arm about a curved path.
Figures 12B, 12C:
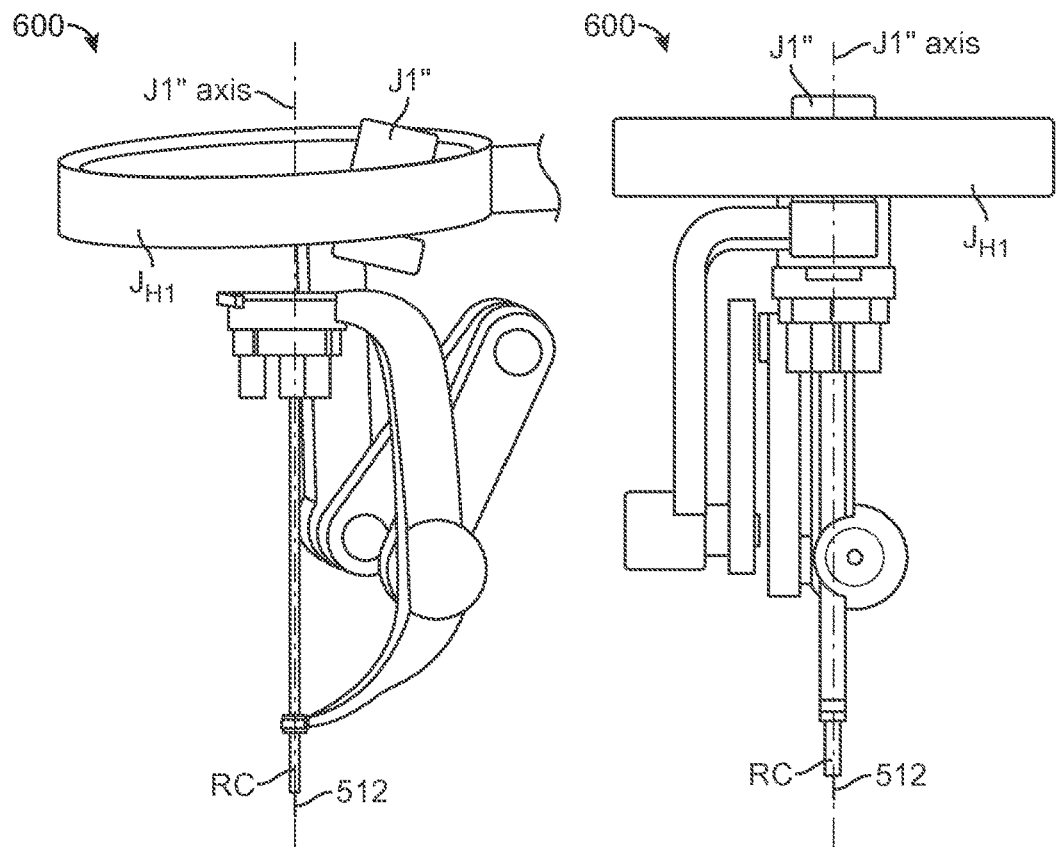
Figure 13A:
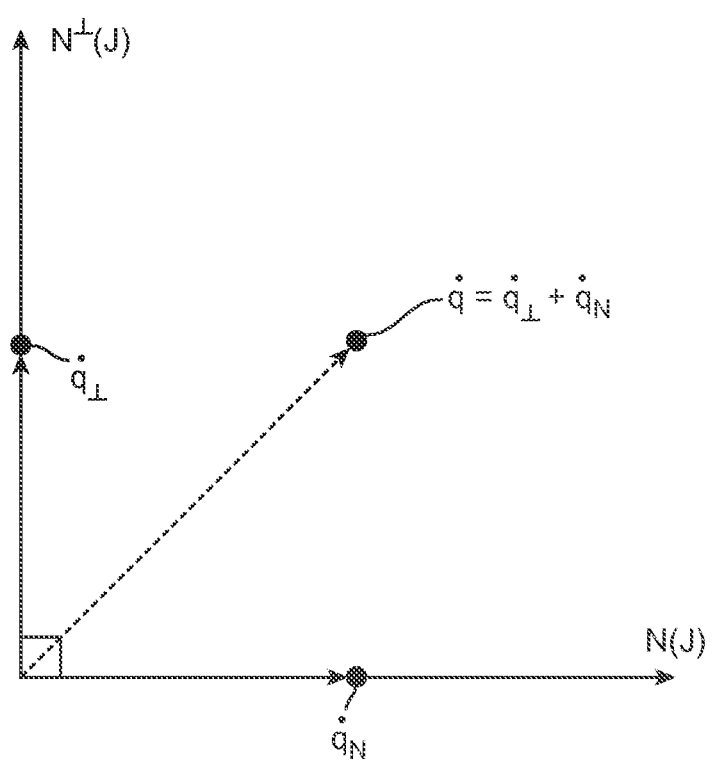
FIGS. 13A-13B graphically represent the relationship between the null-space and the null-perpendicular-space of the Jacobian of an exemplary manipulator assembly.
Figure 13B:
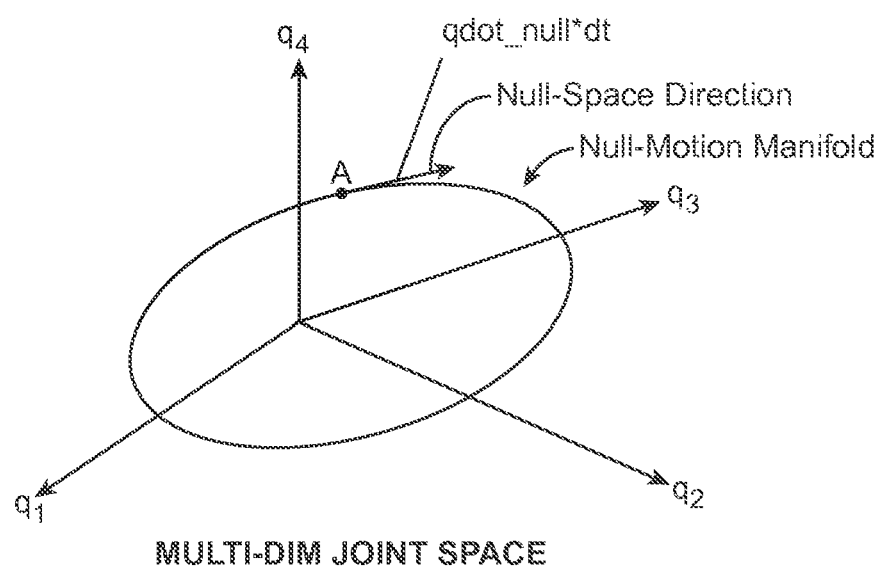

FIGS. 12A-12C illustrate another type of redundant joint for use with exemplary manipulator arms, a proximal joint that translates or revolves the manipulator arm about an axis. In many embodiments, this proximal translatable joint translates a proximal joint of the manipulator, such as joint J1 or J1', along a path so as to reduce or eliminate the cone of silence by shifting or rotating the range of motion of the manipulator arm to provide for better conditioning and improved maneuverability of the manipulator arm. The translatable joint may include a circular path, such as shown in joint J1" in FIGS. 12A-12D, or may include a semi-circular or arcuate path, such as shown in FIGS. 13A-13C. Generally, the joint revolves the manipulator arm about an axis of the translatable joint that intersects with the remote center RC about which the shaft of the tool 512 extending through cannula 511 pivots. Although in the embodiment shown in FIGS. 12A-12C, the axis of J1" is a vertical axis, it is appreciated that the axis of J1" may be horizontal or disposed at various angles of inclination.

In certain embodiments, the manipulator arm 500 may include any or all of a proximal or distal revolute joint, a proximal translatable joint and a parallelogram configuration of the distal linkages. Use of any or all of these features provide additional redundant degrees of freedom and facilitate reconfiguration in accordance with the present invention so as to provide for a better "conditioned" manipulator assembly by increasing the angles between linkages thereby improving the dexterity and motion of the manipulator. The increased flexibility of this exemplary manipulator can also be used to optimize the kinematics of the manipulator linkage so as to avoid joint limits, singularities, and the like.

In certain aspects, the joint movements of the manipulator are controlled by driving one or more joints by a controller using motors of the system, the joints being driven according to coordinated and joint movements calculated by a processor of the controller. Mathematically, the controller may perform at least some of the calculations of the joint commands using vectors and/or matrices, some of which may have elements corresponding to configurations or velocities of the joints. The range of alternative joint configurations available to the processor may be conceptualized as a joint space. The joint space may, for example, have as many dimensions as the manipulator has degrees of freedom, and a particular configuration of the manipulator may represent a particular point in the joint space, with each coordinate corresponding to a joint state of an associated joint of the manipulator.

In one aspect, the system includes a controller in which a commanded position and velocity of a feature in the workspace, denoted here as its Cartesian space, are inputs. The feature may be any feature on the manipulator or off the manipulator which can be used as a control frame to be articulated using control inputs. An example of a feature on the manipulator, used in many examples described herein, would be the tool-tip. Another example of a feature on the manipulator would be a physical feature which is not on the tool-tip, but is a part of the manipulator, such as a pin or a painted pattern. An example of a feature off the manipulator would be a reference point in empty space which is exactly a certain distance and angle away from the tool-tip. Another example of a feature off the manipulator would be a target tissue whose position relative to the manipulator can be established. In all these cases, the end effector is associated with an imaginary control frame which is to be articulated using control inputs. However, in the following, the "end effector" and the "tool tip" are used synonymously. Although generally, there is no closed form relationship which maps a desired Cartesian space end effector position to an equivalent joint-space position, there is generally a closed form relationship between the Cartesian space end effector and joint-space velocities. The kinematic Jacobian is the matrix of partial derivatives of Cartesian space position elements of the end effector with respect to joint space position elements. In this way, the kinematic Jacobian captures the kinematic relationship between the end effector and the joints. In other words, the kinematic Jacobian captures the effect of joint motion on the end effector. The kinematic Jacobian (J) can be used to map joint-space velocities (dq/dt) to Cartesian space end effector velocities (dx/dt) using the relationship below:

$$dx/dt = J\, dq/dt$$

Thus, even when there is no closed-form mapping between input and output positions, mappings of the velocities can iteratively be used, such as in a Jacobian-based controller to implement a movement of the manipulator from a commanded user input, however a variety of implementations can be used. Although many embodiments include a Jacobian-based controller, some implementations may use a variety of controllers that may be configured to access the Jacobian of the manipulator arm to provide any of the features described herein.

One such implementation is described in simplified terms below. The commanded joint position is used to calculate the Jacobian (J). During each time step ($\Delta t$) a Cartesian space velocity (dx/dt) is calculated to perform the desired move ($dx_{des}/dt$) and to correct for built up deviation ($\Delta x$) from the desired Cartesian space position. This Cartesian space velocity is then converted into a joint-space velocity (dq/dt) using the pseudo-inverse of the Jacobian ($J^\#$). The resulting joint-space commanded velocity is then integrated to produce joint-space commanded position (q). These relationships are listed below:

$$dx/dt = dx_{des}/dt + k\Delta x \tag{1}$$

$$dq/dt = J^\# dx/dt \tag{2}$$

$$q_i = q_{i-1} + dq/dt\, \Delta t \tag{3}$$

The pseudo-inverse of the Jacobian (J) directly maps the desired tool tip motion (and, in some cases, a remote center of pivotal tool motion) into the joint velocity space. If the manipulator being used has more useful joint axes than tool tip degrees of freedom (e.g. up to six degrees of freedom), then the manipulator is said to be redundant. For example, when a remote center of tool motion is in use, the manipulator should have an additional 3 joint axes for the 3 degrees of freedom associated with location of the remote center. A redundant manipulator's Jacobian includes a "null-space" having a dimension of at least one. In this context, the "null-space" of the Jacobian (N(J)) is the space of joint velocities which instantaneously achieves no tool tip motion (and when a remote center is used, no movement of the pivotal point location); and "null-motion" is the combination, trajectory or path of joint positions which also produces no instantaneous movement of the tool tip and/or location of the remote center. Incorporating or injecting the calculated null-space velocities into the control system of the manipulator to achieve the desired reconfiguration of the manipulator (including any reconfigurations described herein) changes above equation (2) to the following:

$$dq/dt = dq_{perp}/dt + dq_{null}/dt \tag{4}$$

$$dq_{perp}/dt = J^\# dx/dt \tag{5}$$

$$dq_{null}/dt = (1 - J^\# J)z = V_n V_n^T z = V_n \alpha \tag{6}$$

The joint velocity according to Equation (4) has two components: the first being the null-perpendicular-space component, the "purest" joint velocity (shortest vector length) which produces the desired tool tip motion (and when the remote center is used, the desired remote center motion); and the second being the null-space component. Equations (2) and (5) show that without a null-space component, the same equation is achieved. Equation (6) starts with a traditional form for the null-space component on the left, and on the far right side, shows the form used in an exemplary system, wherein ($V_n$) is the set of orthonormal basis vectors for the null-space, and ($\alpha$) are the coefficients for blending those basis vectors. In some embodiments, $\alpha$ is determined by control parameters, variables or setting, such as by use of knobs or other control means, to shape or control the motion within the null-space as desired.

Figure 14:
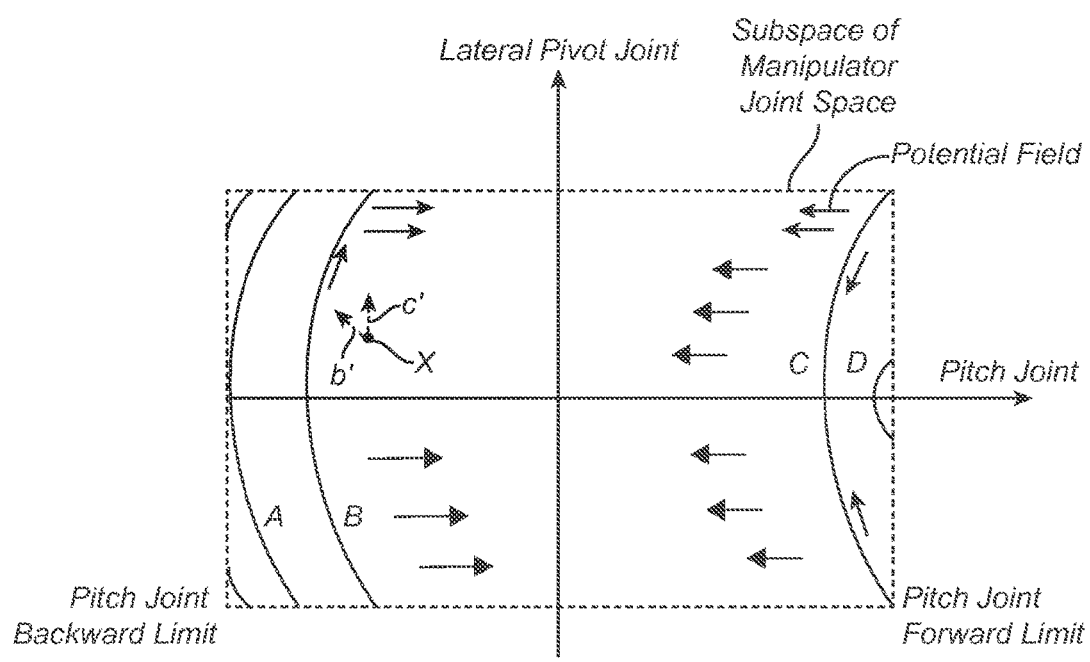
FIG. 14 graphically illustrates an example of network path segments for use in controlling movement of a manipulator assembly within the null-space.

FIG. 13A graphically illustrates the relationship between the null-space of the Jacobian and the null-perpendicular-space of the Jacobian. FIG. 14 shows a two-dimensional schematic showing the null-space along the horizontal axis, and the null-perpendicular-space along the vertical axis, the two axes being orthogonal to one another. The diagonal vector represents the sum of a velocity vector in the null-space and a velocity vector in the null-perpendicular-space, which is representative of Equation (4) above.

FIG. 13B graphically illustrates the relationship between the null-space and the null-motion manifold within a four-dimensional joint space, shown as the "null-motion manifold." Each arrow ($q1$, $q2$, $q3$, and $q4$) representing a principal joint axis. The closed curve represents a null-motion manifold which is a set of joint-space positions which instantaneously achieves the same end effector position. For a given point A on the curve, since the null-space is a space of joint velocities which instantaneously produce no movement of the end effector, the null-space is parallel to the tangent of the null-motion manifold at point A.

FIG. 14 graphically illustrates the two-dimensional subspace of the joint-space of an exemplary manipulator arm. The horizontal and vertical axes represent the movement of two joints having independent joint movement, in particular, movement of joint affecting a pitch of an instrument holder of the manipulator arm (horizontal-axis) versus movement of a distal revolute joint that pivots the instrument holder laterally in either direction from a plane through which a proximal portion of the manipulator arm extends (vertical-axis). The far right side of the subspace represents the forward pitch limit of the pitch joint and the far left side represents the backward pitch limit of the pitch joint. The defined pathways near, curves A, B and C, D, near the forward and backward pitch limits of the pitch joint, respectively, illustrate joint-states of joint movement within a null-space of the Jacobian of the joints of the manipulator arm. For example, for a given end effector state, a controller can move the lateral pivot joint and the pitch joint along each of curves A, B, C and D to increase the range of joint space orthogonal to curves A, B, C and D while maintaining the desired state of the end effector.

The curved lines, A, B, C shown in FIG. 14 indicate joint-space values within the joint-space that lead to a substantially constant Cartesian-space pitch. Each curve is a null-motion manifold, as described in FIG. 13B. During operation of the particular manipulator arm represented by the joint-space in FIG. 14, a greater number of path curves can be traversed in a forward pitch by approaching the horizontal axis (e.g. angular displacement of the lateral pivotal joint approaches zero degrees). Alternatively, a greater number of path curves can be traversed in a backward pitch by approaching the upper and lower corners of the joint-space (e.g. angular displacement of the lateral pivotal joint approaches its ±extrema).

As can be seen in FIG. 14, the Cartersian-coordinate joint space of the represented manipulator arm has four corners. In general, for the joints of the manipulator arm to access the four corners, a controller effecting movement of the joints points toward the corners. In one aspect, a controller calculates movement within a null-space of the Jacobian to move the joints along one or more paths in a joint-space, such as the curves within the joint-space shown in FIG. 14, to improve access of the manipulator arm to the far corners of the Cartesian-coordinate space. In one approach, a potential field is defined within a joint sub-space of the manipulator arm to move the joints along family of curves are used to be able to reach the edges and corners of the joint space, or joint limits in various joint combinations, and in particular the far reaches of the Cartesian-coordinate space. Cartesian-space reaches represented by the pitch joint and the lateral pivotal joint ranges within the joint space are shown in FIG. 14.

One way to define the potential field, which is shown in FIG. 14, is as follows:

$$C = \tfrac{1}{2}(q_{pitch} - q_{pitch-setpoint})^2$$

$$z = (dC/dt)^T = \partial C/\partial q * dq/dt = (q_{pitch} - q_{pitch-setpoint}) * dq/dt$$

where z is then used in equation (6) above.

Alternatively, in certain aspects, an augmented Jacobian that incorporates a potential function gradient and is applied to the Cartesian Space end effector velocities may be used. The augmentation of the Jacobian calculates the joint velocities as desired. It is understood that in referring to calculating joint movements using the Jacobian, such calculations may include the augmented Jacobian approach. In accordance with the augmented Jacobian approach, the following equations may be used, although it is appreciated that column vectors may be used:

$$dx/dt = J * dq/dt$$

$$y = h(q)$$

$$dy/dt = \partial h/\partial q * dq/dt$$

$$[dx/dt^T\ dy/dt^T]^T = [J^T\ \partial h/\partial q^T]^T * dq/dt$$

$$d(x;y)/dt = [J;h'] * dq/dt$$

$$dq/dt = [J;h']^{\#} d(x;y)/dt$$

In one example, the system is configured to set $y=h(q)$ the complex network of potential field functions. The $dy/dt = \partial h/\partial q * dq/dt$. $dy/dt$ and $\partial h/\partial q$ and $dy/dt$ can be dictated as desired based on the potential field functions, and the augmented equation would produce the combined desired result of both driving the end effector and tracking the paths in joint space.

The controller may move the joints orthogonal to paths A, B, C and D using a pseudo-inverse of the Jacobian so as to effect movement of the joints within a null-perpendicular space according to a commanded end effector displacing movement to effect a desired end effector manipulation movement. As the pitch of the pitch joint moves along the horizontal-axis during commanded end effector movement, the system determines movements of the joints positions within a null-space to increase the range of joint space. As shown in FIG. 14 for example, as movement of the pitch joint moves toward the backward limit, the system may determine and effect displacing movement of the lateral pivot joint within the null-space along the nearest curve (see arrow along curve B in FIG. 14) so as to increase the range of joint motion within the null-perpendicular space by increasing the orthogonal distance between the curved path and the limits of the manipulator joint space. For example, in joint space shown in FIG. 14, as the pitch joint moves toward the forward pitch joint limit, the system may determine and effect movement of the lateral pivot joint toward a non-displaced position so as to increase the range of motion within the null-perpendicular space by increasing the orthogonal distance between curved paths (C and D) and the pitch joint forward limit. A virtual potential field space may be used in the joint space to allow for determination of a virtual force that can be used to determine joint velocities to effect the desired movement of the joints within the joint space.

In certain embodiments, the manipulator arm uses a parallelogram linkage in which joints J3, J4 and J5 are configured with interrelated movement to maintain the parallelogram formed by joints J3, J4, J5 and pivot point PP (see for example FIG. 5A). Due to this interrelated movement, the pitch of the instrument shaft may be determined by the state of a pitch joint (e.g. J3). Movement of the pitch joint, such as joint J3 in FIG. 5A, changes the pitch of the insertion axis from a pitch forward position (see FIG. 6A) to a pitch back position (see FIG. 6B). In various other embodiments, the pitch joint may include one or more joints of a manipulator arm the movement of which determines the pitch of the instrument shaft. Movement of the distal revolute joint, such as distal revolute joint J7 supporting the instrument holder 510 and associated cannula 511, pivots or twists the instrument shaft extending through instrument holder 510 laterally relative to a plane through which the portion of the manipulator arm proximal of joint J7 extends. The sub-space of the manipulator joint space illustrates the range of possible combinations of joint states for the pitch joint, J3, and the revolute joint, J7. Although in this embodiment, the positional constraints are defined within a subspace of the joint space defined by the pitch joint and the distal revolute joint described above, it is appreciated that the subspace may be defined by various other joints or by three or more joints.

In the embodiment shown, the movement along the curved paths includes relative movement of the distal revolute joint and pitch joint so that movement of the pitch joint to an increased pitch back position corresponds to increased rotational displacement of the revolute joint, and movement of the pitch joint to a pitch forward position corresponds to minimal or zero displacement of the distal revolute joint. As the outer pitch joint is pitched back, the tool tip on the instrument shaft moves forward. If the outer pitch joint reaches its limit in the pitch-back position, forward movement of a tool tip on the end of the instrument shaft 512 can still be achieved by movement of the distal revolute joint J7. It may be useful however, to initiate movement of the distal revolute joint, J7, as the outer pitch joint J3 approaches its limit in the pitch-back position. Similarly, in the pitch-forward direction, which causes tool tip motion in the backwards direction, the most backward tool tip positioning can be obtained when the movement of the distal revolute joint is minimal, which is at zero angular displacement of the distal revolute joint.

In one aspect, at any point in time, being on any of the paths or curves coincides with meeting a one-dimensional constraint requiring a one-dimensional null-space. This two-dimensional subspace of manipulator joint space can be used to direct the movement of the manipulator arm to the desired positional path by creating an attractive potential field which tends to "pull" or direct the position X of the subject joint states toward or along the defined paths, typically along the path. The system may be configured so that the access facilitating movement of the joints causes the specified joints to move along the defined path segments or may use various magnitudes of attraction within the potential field to cause the joints to along the defined path so as to provide increased range of movement within the joint space of at least one of the joints for a given state of the joints of the manipulator.

In one approach, this is accomplished by generating a potential field in joint-space, such that high potentials represent shorter distances between the X (e.g. the current or calculated manipulator position) and the positional constraint (e.g., the network of paths), and lower potentials represent larger distances. The null-space coefficients ($\alpha$) are then calculated to descend down the negative gradient of the potential field, preferably to the greatest extent possible. In some embodiments, a potential associated with each path (e.g., b' and c') is determined from a distance between the calculated position of the one or more manipulator joints and the defined paths. In response to the calculated attractive force of the artificial potential field on the current joint positions, the system calculates movement of one or more joints of the manipulator arm within the null-space.

While the constraints may be defined as three segments A, B and C within a subspace defined by a distal revolute joint and an outer pitch joint as shown in FIGS. 14A-14C, it is appreciated that the above noted advantages are associated with certain kinematics of a given manipulator arm. Thus, as the kinematics may differ between manipulator arms, so may the desired joint movements and the configuration constraints differ between manipulator arms. For example, depending on the design of a manipulator arm, it may be useful to define the subspace in which the positional constraints are defined by two or more other joints of the manipulator arm. For example, assuming an N-dimensional null-space, a network of N-dimensional manifolds in any dimensional subspace of the full joint space may be defined. In a first example, in a one or more dimensional null-space, a network of one-dimensional curves or line segments may be defined in the entire joint space or in any subspace of therein. Attractive potentials or velocities may then be calculated and projected onto the null-space to determine the access facilitating movement so that a position of the one or more joints corresponds to the defined paths that provide increased range of joint movement, thereby facilitating access to the edges of joints limits of the joint space for one or more joints. In a second example, assuming a null-space of two or more dimensions, a network of two-dimensional surfaces may be defined in the entire joint space or in any subspace therein. Again, attractive potentials or velocities may then be calculated and projected on the null-space as described above. In both examples, the approach causes the manipulator to follow the network of paths, or surfaces rather, to produce the desired movement. In a third example, assuming a null-space of one dimension, a network of two-dimensional surfaces could still be defined in the entire joint space or in a subspace thereof, however, mapping velocities or attractive potentials onto the null-space may provide limited capability in following the network surfaces.

In certain aspects, the approach includes defining positional constraints, such as in a joint-space or in the Cartesian-coordinate space of the tool tip (or some other portion of the manipulator and may include a remote center, such as found in either a hardware or software center system). For a manipulator with n-DOF of redundancy, an n-dimensional null-space of up to n constraints can be satisfied simultaneously). For a case having one-dimensional constraints, this may include a set of piece-wise continuous constraints. One or more paths (e.g. series of curves) may be used to define a network of paths in either the joint-space of the Cartesian-coordinate space. The network of paths may be either static or may be dynamically redefined during the course of surgery. A static network path may be defined at start-up or may be selected by a user or the system from a plurality of static network paths, while a dynamic network path may be dynamically redefined by the system, or by a user, during the course of surgery.

Once the curve paths for facilitating access to the edges of Cartesian-space is determined, the movement of the joints of the manipulator arm is calculated so that the position of the one or more joints tracks the curved paths so as to provide the desired movement of the one or more joints. In some embodiments, the joints of the manipulator arm tracks the curved paths based on a virtual or artificial potential field generated for each segment of that path to attract the manipulator to the path. The movement resulting from the calculated potential may then be projected onto the null-space for calculation of null-space coefficient to provide joint velocities that provide the desired range of joint motion within the Cartesian-space.

Figure 15:
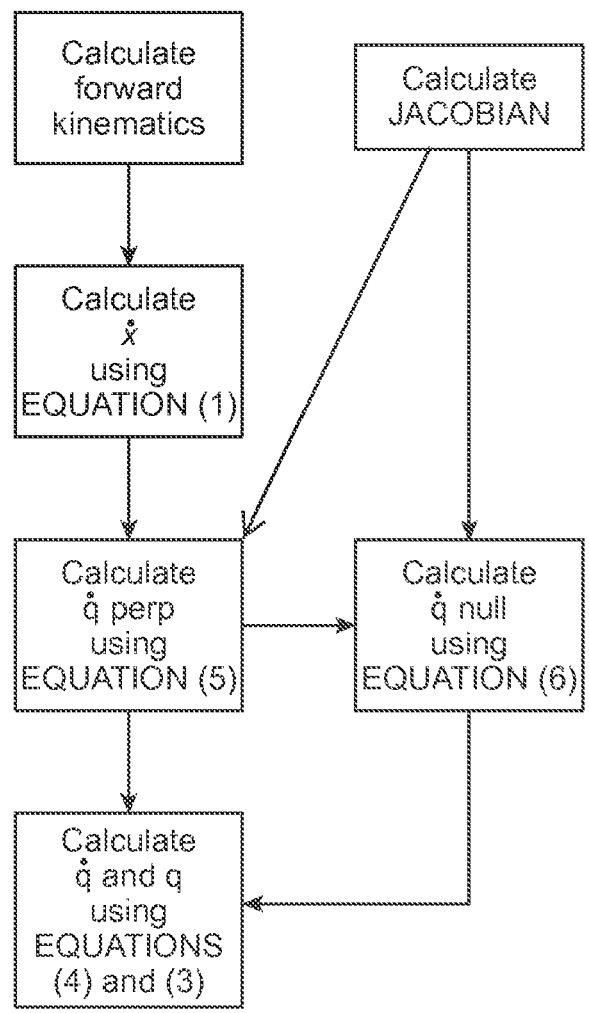
FIGS. 15-17 schematically illustrate methods in accordance an embodiment.
Figure 16:
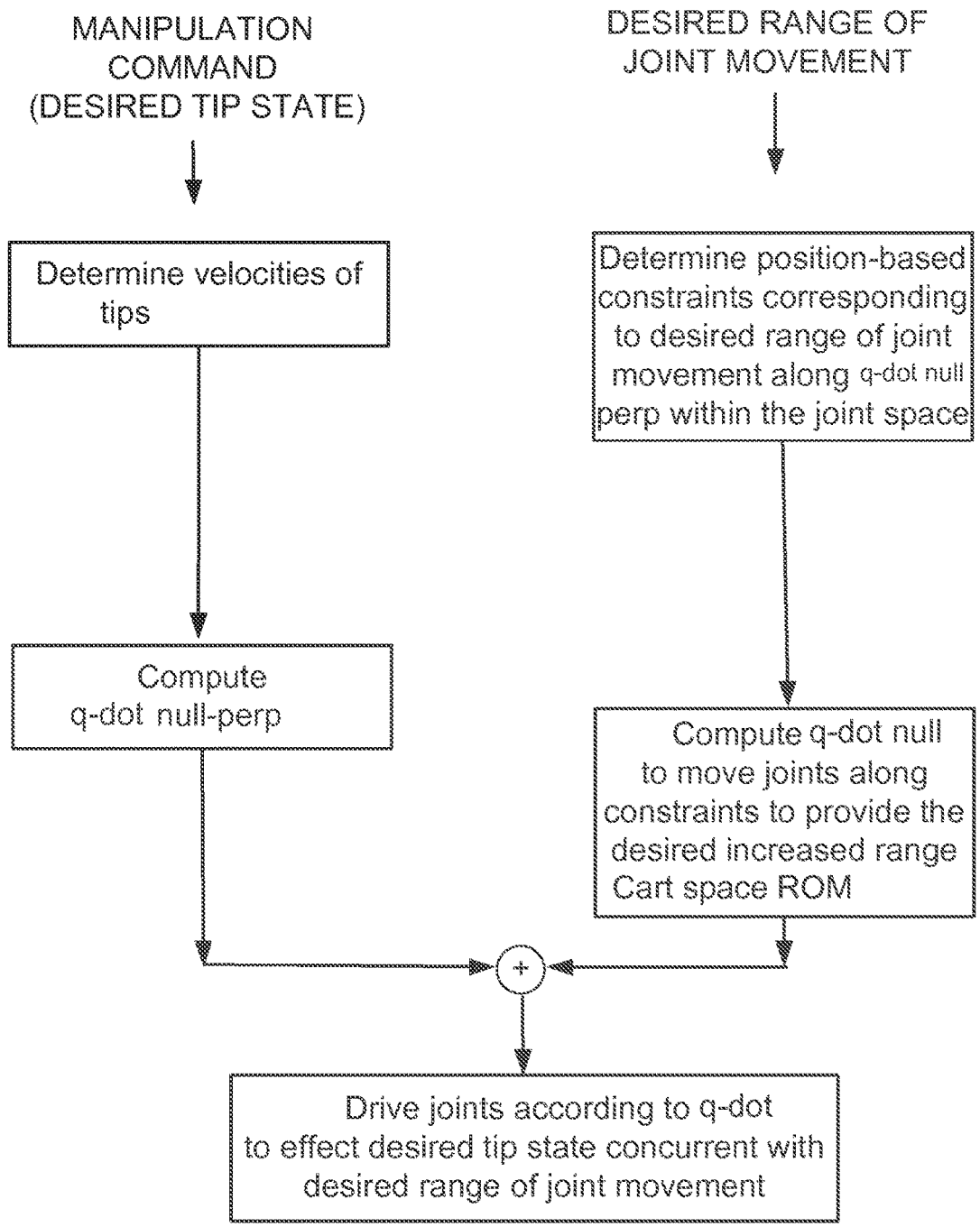

FIGS. 15-16 illustrate methods of reconfiguring a manipulator assembly of a robotic surgical system in accordance with many embodiments of the present invention. FIG. 15 shows a simplified schematic of the required blocks need to implement the general algorithms to control the patient side cart joint states, in relation to the equations discussed above. According to the method of FIG. 15, the system: calculates the forward kinematics of the manipulator arm; then calculates dx/dt using Equation (1), calculates $dq_{perp}/dt$ using Equation (5), then calculates $dq_{null}/dt$ from z which may depend on $dq_{perp}/dt$ and the Jacobian using Equation (6). From the calculated $dq_{perp}/dt$ and $dq_{null}/dt$ the system then calculates dq/dt and q using Equations (4) and (3), respectively, thereby providing the movement by which the controller can effect the desired reconfiguration of the manipulator while maintaining the desired state of the end effector and/or location of the remote center.

FIG. 16 shows a block diagram of an exemplary embodiment of the system. In response to a manipulation command, which commands a desired tool tip state, a processor of the system determines the velocities of the tool tip and the states of the joints from which the $dq_{perp}/dt$ is calculated. To provide an increased range of joint movement for one or more joints of the manipulator arm, the system determined position-based constraints within the subspace of the joints for which controlled movement is desired, such as a series of curved paths representing joint movement within the null-space, the curved paths defined to increase an orthogonal distance between the curved paths and the limits or edges of the joints space, the orthogonal distance corresponding to null-perpendicular movement within the joint space. The $dq_{null}/dt$ is then calculated so as to move the joints within the null-space along the positional constraint, such as through the use of an attractive potential field calculated along a curved path in the joint space, which may be added to the $dq_{perp}/dt$ to calculate dq/dt so as to drive the joint(s) of the system and effect the desired movement (or state) of the end effector while providing an increased range of movement of the one or more joints within the null-perpendicular space as desired.

Figure 17:
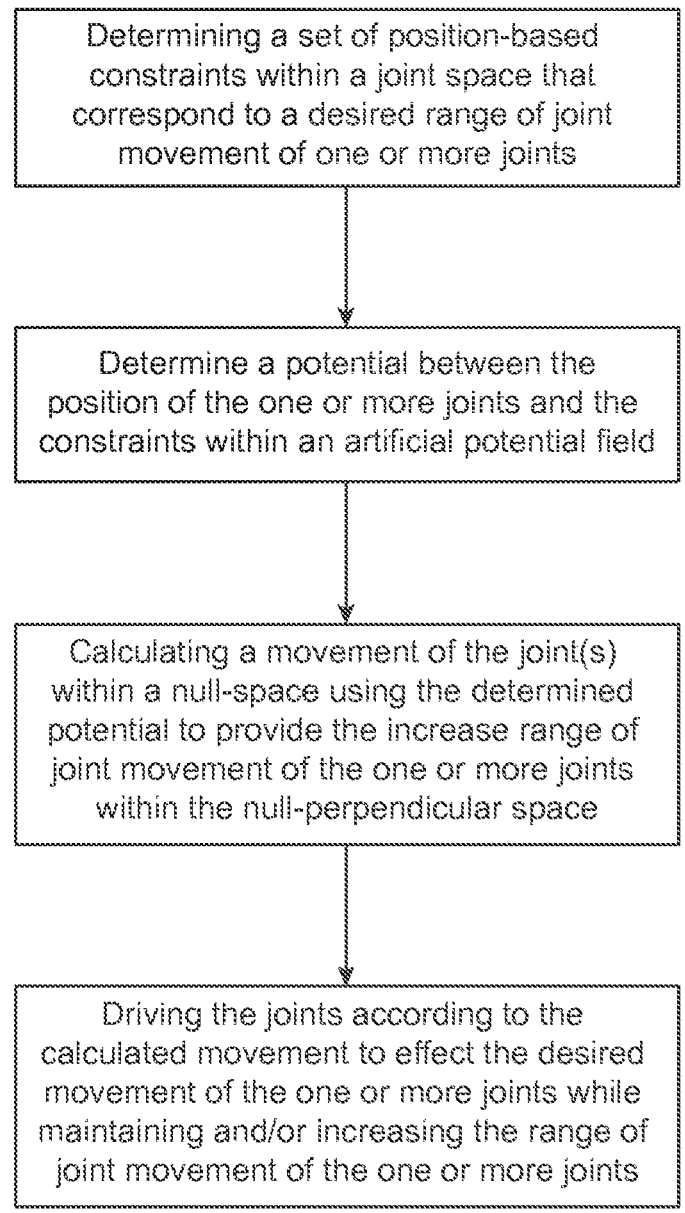

FIG. 17 shows a flow chart of an example method in accordance with aspect of the present invention. The method includes: determining a set of position-based constraints within a joint space that correspond to a desired range of joint movement of one or more joints; determine a potential between the position of the one or more joints and the constraints within an artificial potential field; calculating a movement of the joint(s) within a null-space using the determined potential to provide the increase range of joint movement of the one or more joints within the null-perpendicular space; and driving the joints according to the calculated movement to effect the desired movement of the one or more joints while maintaining and/or increasing the range of joint movement of the one or more joints.

While the exemplary embodiments have been described in some detail for clarity of understanding and by way of example, a variety of adaptations, modifications, and changes will be obvious to those of skill in the art. Hence, the scope of the present invention is limited solely by the appended claims.

What is claimed is:

1. A method for a manipulator arm, the manipulator arm comprising a movable distal portion that includes an end effector, a proximal portion coupled to a base, and a plurality of joints between the distal portion and the base, the plurality of joints having sufficient degrees of freedom to allow a range of differing joint states for a given state of the end effector, the method comprising:
defining a position-based constraint of a first joint of the plurality of joints within a joint space of the plurality of jointsto provide an increased range of movement for the end effector, the position-based constraint including a first path corresponding to differing ranges of movement for the end effector;
calculating a facilitating movement of the plurality of joints along the first path of the position-based constraint, wherein calculating the facilitating movement comprises calculating joint velocities of the plurality of joints from directions that correspond to the end effector not moving; and
driving the plurality of joints according to the calculated facilitating movement so as to provide the increased range of movement for the end effector.

2. The method of claim 1, wherein the position-base constraint comprises one or more surfaces defined within a subspace of the joint space of the plurality of joints, the one or more surfaces including the first path of the position-based constraint, and the subspace being defined by at least two joints of the plurality of joints including the first joint of the plurality of joints.

3. The method of claim 1, further comprising:
receiving a manipulation command to move the end effector with a desired end-effector movement;
calculating an end-effector displacing movement of the plurality of joints to provide the desired end effector movement, wherein calculating the end-effector displacing movement comprises calculating joint velocities of the plurality of joints from directions that correspond to the end effector moving; and
driving the plurality of joints according to the calculated end-effector displacing movement in combination with the calculated facilitating movement so as to provide the desired end-effector movement in combination with the increased range of movement for the end effector.

4. The method of claim 1, further comprising:
calculating values for a Jacobian of the manipulator arm, the joint velocities from directions that correspond to the end effector not moving being associated with a null space of the Jacobian, and the joint velocities from directions that correspond to the end effector moving being associated with a null-perpendicular space of the Jacobian.

5. The method of claim 1, further comprising:
defining a potential field corresponding to the position-based constraint of the first joint of the plurality of joints, the potential field including directions corresponding to improved values for the position-based constraint; and
calculating the facilitating movement of the plurality of joints from directions that correspond to the end effector not moving in combination with improved values for the position-based constraint.

6. The method of claim 1, further comprising:
defining a potential field corresponding to the position-based constraint of the first joint of the plurality of joints, the potential field including directions corresponding to improved values for the position-based constraint; and
calculating the facilitating movement of the plurality of joints by projecting the directions corresponding to improved values for the position-based constraint onto the directions that correspond to the end effector not moving.

7. The method of claim 1, further comprising:
defining an attractive potential function corresponding to the position-based constraint of the first joint of the plurality of joints, the potential function characterizing a degree of satisfaction for the position-based constraint; and
calculating the facilitating movement of the plurality of joints by projecting a gradient of the potential function onto the directions that correspond to the end effector not moving.

8. A system comprising:
a manipulator arm comprising a movable distal portion that includes an end effector, a proximal portion coupled to a base, and a plurality of joints between the distal portion and the base, the plurality of joints having sufficient degrees of freedom to allow a range of differing joint states for a given state of the end effector; and
one or more processors operably connected to the manipulator arm, the one or more processors being configured to perform operations including:
defining a position-based constraint of a first joint of the plurality of joints within a joint space of the plurality of joints to provide an increased range of movement for the end effector, the position-based constraint including a first path corresponding to differing ranges of movement for the end effector;
calculating a facilitating movement of the plurality of joints along the first path of the position-based constraint, wherein calculating the facilitating movement comprises calculating joint velocities of the plurality of joints from directions that correspond to the end effector not moving; and
driving the plurality of joints according to the calculated facilitating movement so as to provide the increased range of movement for the end effector.

9. The system of claim 8, wherein the position-based constraint comprises one or more surfaces defined within a subspace of the joint space of the plurality of joints, the one or more surfaces including the first path of the position-based constraint, and the subspace being defined by at least two joints of the plurality of joints including the first joint of the plurality of joints.

10. The system of claim 8, further comprising an input device for receiving a manipulation command to move the end effector with a desired end-effector movement; wherein the operations further comprise:
calculating an end-effector displacing movement of the plurality of joints to provide the desired end effector movement, wherein calculating the end-effector displacing movement comprises calculating joint velocities of the plurality of joints from directions that correspond to the end effector moving; and
driving the plurality of joints according to the calculated end-effector displacing movement in combination with the calculated facilitating movement so as to provide the desired end-effector movement in combination with the increased range of movement for the end effector.

11. The system of claim 8, wherein the operations further comprise:
calculating values for a Jacobian of the manipulator arm, the joint velocities from directions that correspond to the end effector not moving being associated with a null space of the Jacobian, and the joint velocities from directions that correspond to the end effector moving being associated with a null-perpendicular space of the Jacobian.

12. The system of claim 8, wherein the operations further comprise:
defining a potential field corresponding to the position-based constraint of the first joint of the plurality of joints, the potential field including directions corresponding to improved values for the position-based constraint; and
calculating the facilitating movement of the plurality of joints from directions that correspond to the end effector not moving in combination with improved values for the position-based constraint.

13. The system of claim 8, wherein the operations further comprise:
defining a potential field corresponding to the position-based constraint of the first joint of the plurality of joints, the potential field including directions corresponding to improved values for the position-based constraint; and
calculating the facilitating movement of the plurality of joints by projecting the directions corresponding to improved values for the position-based constraint onto the directions that correspond to the end effector not moving.

14. The system of claim 8, wherein the operations further comprise:
defining an attractive potential function corresponding to the position-based constraint of the first joint of the plurality of joints, the potential function characterizing a degree of satisfaction for the position-based constraint; and
calculating the facilitating movement of the plurality of joints by projecting a gradient of the potential function onto the directions that correspond to the end effector not moving.

15. A non-transitory readable memory storing a processor-implemented program for a manipulator arm, the manipulator arm comprising a movable distal portion that includes an end effector, a proximal portion coupled to a base, and a plurality of joints between the distal portion and the base, the plurality of joints having sufficient degrees of freedom to allow a range of differing joint states for a given state of the end effector, and the processor-implemented program including instructions that, when executed by one or more processors, cause the one or more processors to perform operations comprising:
defining a position-based constraint of a first joint of the plurality of joints within a joint space of the plurality of joints to provide an increased range of movement for the end effector, the position-based constraint including a first path corresponding to differing ranges of movement for the end effector;
calculating a facilitating movement of the plurality of joints along the first path of the position-based constraint, wherein calculating the facilitating movement comprises calculating joint velocities of the plurality of joints from directions that correspond to the end effector not moving; and driving the plurality of joints according to the calculated facilitating movement so as to provide the increased range of movement for end effector.

16. The readable memory of claim 15, wherein the position-based constraint comprises one or more surfaces defined within a subspace of the joint space of the plurality of joints, the one or more surfaces including the first path of the position-based constraint, and the subspace being defined by at least two joints of the plurality of joints including the first joint of the plurality of joints.

17. The readable memory of claim 15, wherein the operations further comprise:

receiving a manipulation command to move the end effector with a desired end-effector movement;

calculating an end-effector displacing movement of the plurality of joints to provide the desired end effector movement, wherein calculating the end-effector displacing movement comprises calculating joint velocities of the plurality of joints from directions that correspond to the end effector moving; and driving the plurality of joints according to the calculated end-effector displacing movement in combination with the calculated facilitating movement so as to provide the desired end-effector movement in combination with the increased range of movement for the end effector.

18. The readable memory of claim 15, wherein the operations further comprise:

calculating values for a Jacobian of the manipulator arm, the joint velocities from directions that correspond to the end effector not moving being associated with a null space of the Jacobian, and the joint velocities from directions that correspond to the end effector moving being associated with a null-perpendicular space of the Jacobian.

19. The readable memory of claim 15, wherein the operations further comprise:

defining a potential field corresponding to the position-based constraint of the first joint of the plurality of joints, the potential field including directions corresponding to improved values for the position-based constraint; and calculating the facilitating movement of the plurality of joints from directions that correspond to the end effector not moving in combination with improved values for the position-based constraint.

20. The readable memory of claim 15, wherein the operations further comprise:

defining a potential field corresponding to the position-based constraint of the first joint of the plurality of joints, the potential field including directions corresponding to improved values for the position-based constraint; and calculating the facilitating movement of the plurality of joints by projecting the directions corresponding to improved values for the position-based constraint onto the directions that correspond to the end effector not moving.

* * * * *